US012564725B2

(12) United States Patent
Uchitel et al.

(10) Patent No.: US 12,564,725 B2
(45) Date of Patent: Mar. 3, 2026

(54) TREATMENT OF INTERNAL SPACES USING PLASMA GENERATING DEVICE

(71) Applicant: CAPS Medical Ltd., Netanya (IL)

(72) Inventors: Ilan Oleg Uchitel, Kfar-Saba (IL); Boris Kogan, Kiriat-Motzkin (IL)

(73) Assignee: CAPS Medical Ltd., Netanya (IL)

( * ) Notice: Subject to any disclaimer, the term of this patent is extended or adjusted under 35 U.S.C. 154(b) by 836 days.

(21) Appl. No.: 17/912,593

(22) PCT Filed: Mar. 18, 2021

(86) PCT No.: PCT/IL2021/050303
§ 371 (c)(1),
(2) Date: Sep. 19, 2022

(87) PCT Pub. No.: WO2021/186449
PCT Pub. Date: Sep. 23, 2021

(65) Prior Publication Data
US 2023/0132232 A1 Apr. 27, 2023

Related U.S. Application Data

(60) Provisional application No. 62/991,649, filed on Mar. 19, 2020.

(51) Int. Cl.
*A61N 1/44* (2006.01)
*A61M 13/00* (2006.01)
(Continued)

(52) U.S. Cl.
CPC ............. *A61N 1/44* (2013.01); *A61M 13/003* (2013.01); *A61M 25/1011* (2013.01); *A61M 2039/242* (2013.01)

(58) Field of Classification Search
CPC ... A61N 1/44; A61M 13/003; A61M 25/1011; A61M 2039/242
(Continued)

(56) References Cited

U.S. PATENT DOCUMENTS 5,720,745 A * 2/1998 Farin .................... A61B 18/042
606/49
6,213,999 B1 4/2001 Platt, Jr. et al.
(Continued)

FOREIGN PATENT DOCUMENTS

CN 102646569 8/2012
CN 203634283 6/2014
(Continued)

OTHER PUBLICATIONS

Communication Pursuant to Article 94(3) EPC Dated Mar. 3, 2025 From the European Patent Office Re. Application No. 21717564.5 (6 Pages).
(Continued)

*Primary Examiner* — Phillip A Gray

(57) ABSTRACT

Plasma delivery tips of medical-grade plasma generating devices are configured to exclude potential contaminants while operating within body cavities. In some embodiments, delivery tips are provided with an antechamber, which is optionally filled by pressure of ionizing gas to prevent contamination. Some embodiments are provided with one or more interior and/or exterior valves configured to prevent proximal ingress of contamination to the longitudinal position of the discharge electrode, or at all into the gas delivery lumen. In some embodiments, an expandable distal section of the plasma delivery tip acts as a valve which seals when closed, and when open expands to generate an inflated antechamber into which plasma is delivered.

20 Claims, 16 Drawing Sheets

(51) Int. Cl.
| | | |
|---|---|---|
| *A61M 25/10* | (2013.01) | |
| *A61M 39/24* | (2006.01) | |

(58) Field of Classification Search
USPC .......................................................... 604/21
See application file for complete search history.

(56) References Cited

U.S. PATENT DOCUMENTS

| | | | |
|---|---|---|---|
| 6,262,386 | B1 | 7/2001 | Foernsel |
| 6,582,423 | B1 | 6/2003 | Thapliyal |
| 7,578,817 | B2 * | 8/2009 | Canady .............. A61B 18/1442 |
| | | | 606/49 |
| 7,993,339 | B2 * | 8/2011 | Kuhner ................ A61B 18/042 |
| | | | 606/49 |
| 9,186,208 | B2 | 11/2015 | Truckai et al. |
| 9,226,790 | B2 | 1/2016 | Zemel et al. |
| 2002/0187066 | A1 | 12/2002 | Yu |
| 2004/0036397 | A1 | 2/2004 | Kim |
| 2006/0247617 | A1 | 11/2006 | Danek et al. |
| 2007/0225700 | A1 | 9/2007 | Kuhner |
| 2009/0076505 | A1 | 3/2009 | Arts |
| 2009/0121637 | A1 | 5/2009 | Laroussi |
| 2010/0100091 | A1 | 4/2010 | Truckai |
| 2012/0029506 | A1 | 2/2012 | Johnson |
| 2012/0080412 | A1 | 4/2012 | Holbeche et al. |
| 2012/0107896 | A1 | 5/2012 | Wandke et al. |
| 2012/0197245 | A1 | 8/2012 | Burnett et al. |
| 2012/0229029 | A1 | 9/2012 | Takenoshita et al. |
| 2013/0153545 | A1 | 6/2013 | Kim et al. |
| 2013/0218069 | A1 | 8/2013 | Neugebauer et al. |
| 2013/0304060 | A1 | 11/2013 | Truckai et al. |
| 2014/0005481 | A1 | 1/2014 | Rontal et al. |
| 2014/0316403 | A1 | 10/2014 | Konesky et al. |
| 2015/0038790 | A1 | 2/2015 | Rontal et al. |
| 2015/0151135 | A1 | 6/2015 | Kalghatgi |
| 2015/0366042 | A1 | 12/2015 | Zaidi |
| 2016/0121134 | A1 | 5/2016 | Kalghatgi et al. |
| 2016/0361558 | A1 | 12/2016 | Jacofsky et al. |
| 2017/0128117 | A1 | 5/2017 | Myers et al. |
| 2017/0246440 | A1 | 8/2017 | Kalghatgi et al. |
| 2017/0354453 | A1 | 12/2017 | Krasik et al. |
| 2018/0318459 | A1 | 11/2018 | Hancock et al. |
| 2019/0083159 | A1 | 3/2019 | Hancock et al. |
| 2019/0269450 | A1 | 9/2019 | Hancock et al. |
| 2023/0125601 | A1 | 4/2023 | Uchitel |
| 2023/0125841 | A1 | 4/2023 | Uchitel |
| 2023/0126911 | A1 | 4/2023 | Uchitel |

FOREIGN PATENT DOCUMENTS

| | | |
|---|---|---|
| CN | 105009691 | 10/2015 |
| CN | 110200695 | 9/2019 |
| EP | 1090598 | 9/2005 |
| EP | 3422981 | 1/2019 |
| GB | 2521611 | 7/2015 |
| GB | 2547941 | 9/2017 |
| JP | 2008-501450 | 1/2008 |
| WO | WO 00/79843 | 12/2000 |
| WO | WO 2005/120372 | 12/2005 |
| WO | WO 2012/178177 | 12/2012 |
| WO | WO 2013/032182 | 3/2013 |
| WO | WO 2013/040542 | 3/2013 |
| WO | WO 2016/036927 | 3/2016 |
| WO | WO 2016/071680 | 5/2016 |
| WO | WO 2016/607680 | 5/2016 |
| WO | WO 2016/083539 | 6/2016 |
| WO | WO 2017/005830 | 1/2017 |
| WO | WO 2017/087578 | 5/2017 |
| WO | WO 2017/149072 | 9/2017 |
| WO | WO 2018/178252 | 10/2018 |
| WO | WO 2019/089392 | 5/2019 |
| WO | WO 2019/211276 | 11/2019 |
| WO | WO 2021/186448 | 9/2021 |
| WO | WO 2021/186449 | 9/2021 |
| WO | WO 2021/186450 | 9/2021 |
| WO | WO 2021/186451 | 9/2021 |
| WO | WO 2021/186450 A9 | 10/2021 |

OTHER PUBLICATIONS

Communication Pursuant to Article 94(3) EPC Dated Feb. 28, 2025 From the European Patent Office Re. Application No. 21717565.2 (6 Pages).

Notification of Office Action and Search Report Dated Jan. 25, 2025 From the State Intellectual Property Office of the People's Republic of China Re. Application No. 202180029380.X and Its Translation of the Office Action into English. (9 Pages).

Summons to Attend Oral Proceedings Pursuant to Rule 115(1) EPC Dated Nov. 29, 2024 From the European Patent Office Re. Application No. 21717238.6. (10 Pages).

Communication Pursuant to Article 94(3) EPC Dated Oct. 5, 2023 From the European Patent Office Re. Application No. 21717238.6 (7 Pages).

Office Action Dated Mar. 31, 2024 From the Israel Patent Office Re. Application No. 296584. (4 Pages).

Notice of Reasons for Rejection Dated Dec. 17, 2024 From the Japan Patent Office Re. Application No. 2022-556644 and Its Translation Into English. (12 Pages).

English Translation and its Summary Dated Aug. 18, 2024 of Notification of Office Action and Search Report Dated Aug. 15, 2024 From the State Intellectual Property Office of the People's Republic of China Re. Application No. 202180028920.2. (5 Pages).

European Search Report and the European Search Opinion Dated Aug. 7, 2024 From the European Patent Office Re. Application No. 24174609.8. (5 Pages).

Notification of Office Action and Search Report Dated Aug. 15, 2024 From the State Intellectual Property Office of the People's Republic of China Re. Application No. 202180028920.2. (7 Pages).

International Preliminary Report on Patentability Dated May 18, 2022 From the International Preliminary Examining Authority Re. Application No. PCT/IL2021/050305. (19 Pages).

International Preliminary Report on Patentability Dated Jun. 21, 2022 From the International Preliminary Examining Authority Re. Application No. PCT/IL2021/050302. (32 Pages).

International Preliminary Report on Patentability Dated Jun. 22, 2022 From the International Preliminary Examining Authority Re. Application No. PCT/IL2021/050304. (18 Pages).

International Preliminary Report on Patentability Dated Jun. 29, 2022 From the International Preliminary Examining Authority Re. Application No. PCT/IL2021/050303. (32 Pages).

International Search Report and the Written Opinion Dated Jul. 6, 2021 From the International Searching Authority Re. Application No. PCT/IL2021/050305. (21 Pages).

International Search Report and the Written Opinion Dated Oct. 11, 2021 From the International Searching Authority Re. Application No. PCT/IL2021/050302 (24 Pages).

International Search Report and the Written Opinion Dated Aug. 27, 2021 From the International Searching Authority Re. Application No. PCT/IL2021/050304. (21 Pages).

International Search Report and the Written Opinion Dated Sep. 29, 2021 From the International Searching Authority Re. Application No. PCT/IL2021/050303. (23 Pages).

Invitation to Pay Additional Fees, Communication Relating to the Results of the Partial International Search and the Provisional Opinion Dated Jul. 6, 2021 From the International Searching Authority Re. Application No. PCT/IL2021/050304. (13 Pages).

Invitation to Pay Additional Fees, Communication Relating to the Results of the Partial International Search and the Provisional Opinion Dated Jul. 7, 2021 From the International Searching Authority Re. Application No. PCT/IL2021/050302. (14 Pages).

Invitation to Pay Additional Fees, Communication Relating to the Results of the Partial International Search and the Provisional Opinion Dated Jun. 29, 2021 From the International Searching Authority Re. Application No. PCT/IL2021/050303. (12 Pages).

(56)     References Cited

OTHER PUBLICATIONS

Invitation to Restrict or Pay Additional Fees Dated Feb. 3, 2022 From the International Preliminary Examining Authority Re. Application No. PCT/IL2021/050303. (4 Pages).
Invitation to Restrict or Pay Additional Fees Dated Feb. 7, 2022 From the International Preliminary Examining Authority Re. Application No. PCT/IL2021/050302. (4 Pages).
Written Opinion Dated Mar. 11, 2022 From the International Preliminary Examining Authority Re. Application No. PCT/IL2021/050302. (28 Pages).
Written Opinion Dated Mar. 16, 2022 From the International Preliminary Examining Authority Re. Application No. PCT/IL2021/050303. (7 Pages).
Written Opinion Dated Feb. 17, 2017 From the International Preliminary Examining Authority Re. Application No. PCT/IL2021/050304. (20 Pages).
Written Opinion Dated Feb. 21, 2022 From the International Preliminary Examining Authority Re. Application No. PCT/IL2021/050305. (10 Pages).
You et al. "Electrowetting on Non-Fluorinated Hydrophobic Surfaces", Journal of the Society for Information Display, SID, 21(10): 411-416, Oct. 2014.

* cited by examiner

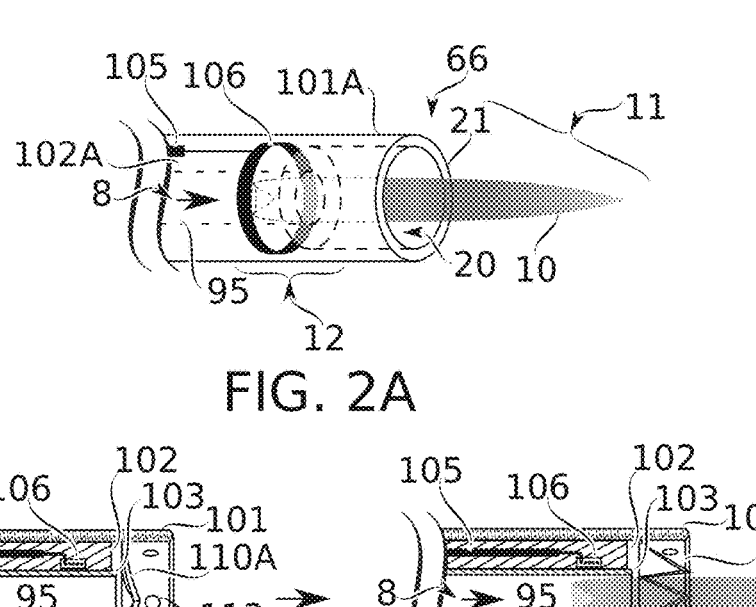
FIG. 2A
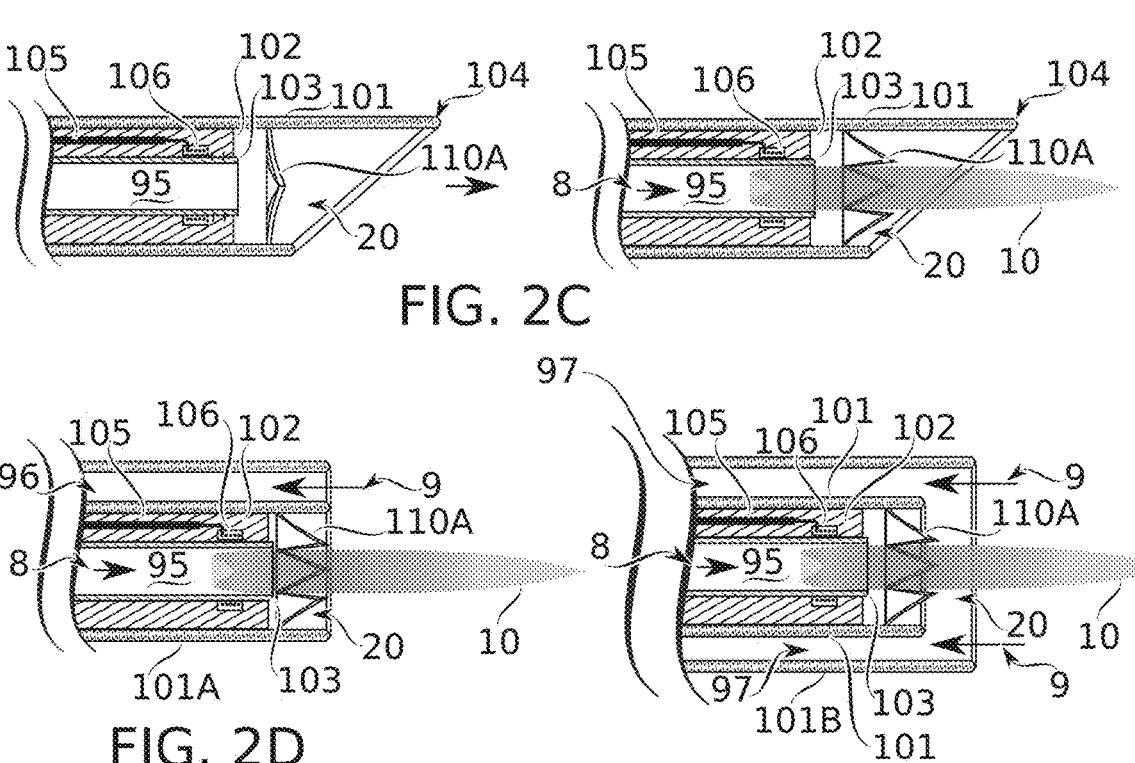
FIG. 2B
FIG. 2C
FIG. 2D
FIG. 2E

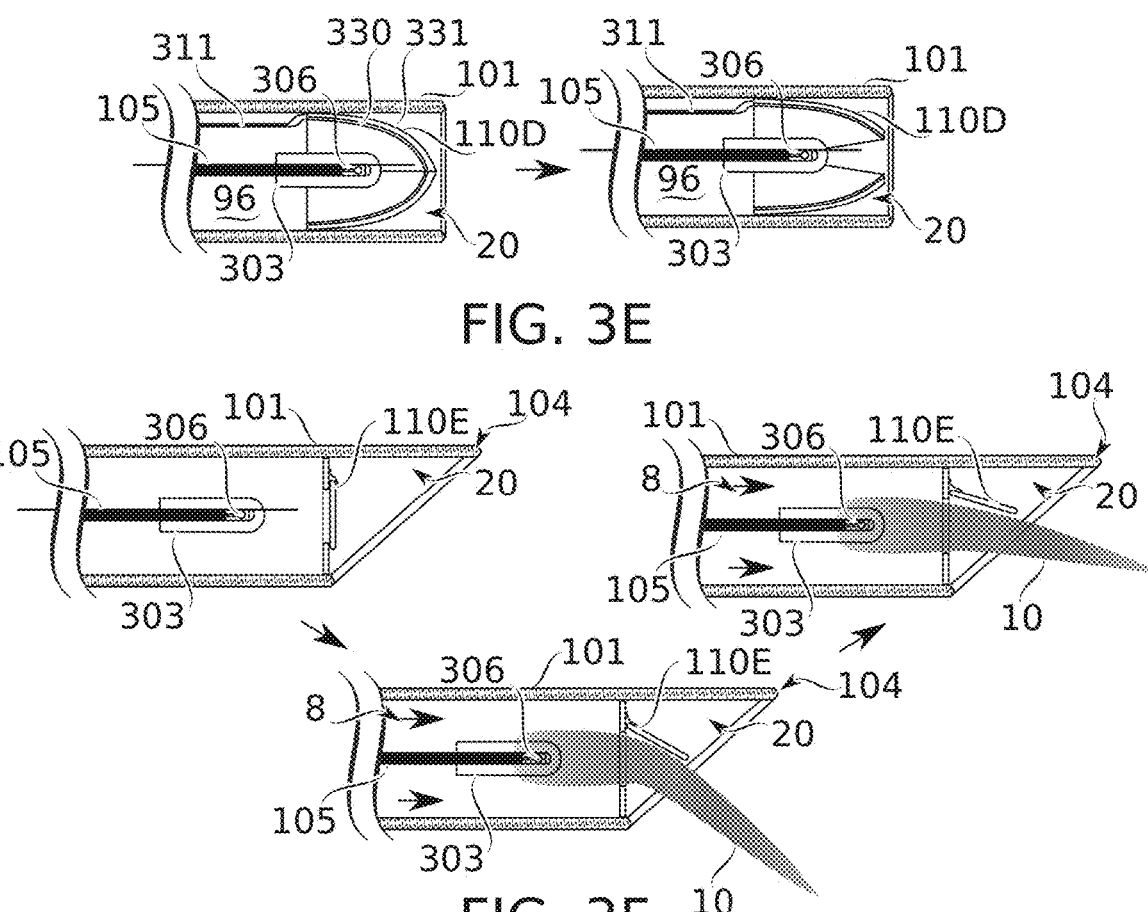
FIG. 3E
FIG. 3F
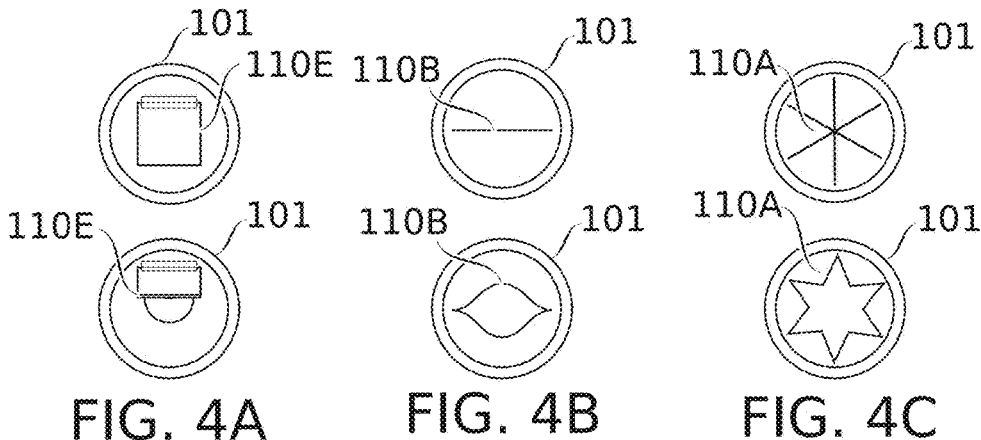
FIG. 4A          FIG. 4B          FIG. 4C

1371 Insert plasma delivery tip into body lumen

1372 Inflate balloons to create sealed lumenal space

1373 Evacuate liquid from lumenal space

1374 Deliver plasma

1375 Restore liquid to lumenal space

1376 Collapse balloons; remove plasma delivery tip from body lumen

TREATMENT OF INTERNAL SPACES USING PLASMA GENERATING DEVICE

RELATED APPLICATIONS

This application is a National Phase of PCT Patent Application No. PCT/IL2021/050303 having International filing date of Mar. 18, 2021, which claims the benefit of priority under 35 USC § 119 (e) of U.S. Provisional Patent Application No. 62/991,649 filed on Mar. 19, 2020.

PCT Patent Application No. PCT/IL2021/050303 is one of four co-filed applications including PCT Patent Applications Nos. PCT/IL2021/050305, PCT/IL2021/050304, and PCT/IL2021/050302.

The contents of the above applications are all incorporated by reference as if fully set forth herein in their entirety.

FIELD AND BACKGROUND OF THE INVENTION

The present invention, in some embodiments thereof, relates to the field of cold atmospheric plasma generation and more particularly, to delivery of cold plasma within body cavities.

Plasma is a general term encompassing compositions of ionized gas, generally including free electrons and ions, as well as neutral atoms and molecules, and often free radicals. Plasma may be produced by electric discharge through gas, causing gas atoms or molecules to be excited and ionize. During the past decade, significant interest in plasma applications has grown. Some applications are based on Dielectric Barrier Discharge (DBD) for generation of the non-thermal plasma of low temperature, or so-called "cold" plasma. Such cold plasma is a low-ionized and non-thermal plasma generated at atmospheric pressure conditions. It has been found that cold plasma can be used for various applications in medicine and industry.

SUMMARY OF THE INVENTION

According to an aspect of some embodiments of the present disclosure, there is provided a plasma delivery tip of a medical grade plasma generating device, including: a gas delivery lumen defined within a circumferential wall and having a proximal-to-distal axis, and along which a flow of ionization gas flows to a distal aperture of the gas delivery lumen; a discharge electrode, which transmits a high voltage to the flow of ionization gas when attached to a high voltage source; and a valve, positioned to prevent proximal ingress of contamination to a longitudinal position of the discharge electrode along the proximal-to-distal axis.

According to some embodiments of the present disclosure, the valve, when closed, is also positioned to prevent ingress of liquid material through the aperture.

According to some embodiments of the present disclosure, the valve is positioned within the gas delivery lumen, between the aperture and the discharge electrode.

According to some embodiments of the present disclosure, the valve includes a one-way valve which opens under pressure from the flow of ionization gas.

According to some embodiments of the present disclosure, the valve includes an actuated valve, actuated separately from pressure from the flow of ionization gas.

According to some embodiments of the present disclosure, the aperture of the gas delivery lumen is obliquely angled relative to the proximal-to-distal axis.

According to some embodiments of the present disclosure, the valve includes a leaf valve, a slit valve, or a flap valve.

According to some embodiments of the present disclosure, the valve is configured to deflect a plasma plume generated within the flow of ionization gas by the pulses of high voltage to an angle which varies according to a degree of opening of the valve.

According to some embodiments of the present disclosure, the plasma delivery tip includes an outer circumferential wall surrounding and radially spaced from the circumferential wall of the gas delivery lumen to define a gap through which the ionization gas is scavenged after delivery to the discharge electrode.

According to some embodiments of the present disclosure, the circumferential wall of the gas delivery lumen also defines a conduit through which the ionization gas is scavenged after delivery to the discharge electrode.

According to some embodiments of the present disclosure, the valve, when closed, includes a collapsed antechamber of the gas delivery lumen positioned along the proximal-to-distal axis between the discharge electrode and the aperture.

According to some embodiments of the present disclosure, the antechamber expands to a have an inner diameter at least 1.5 times larger than an inner diameter of the antechamber in the collapsed configuration.

According to some embodiments of the present disclosure, the valve includes a calyx having one or more leaves attached on a proximal side thereof to an exterior of the plasma delivery tip.

According to some embodiments of the present disclosure, the leaves split from each other when expanded to expose the aperture of the gas delivery lumen.

According to some embodiments of the present disclosure, the expanded antechamber defines the aperture of the gas delivery lumen at a distal side of the antechamber.

According to some embodiments of the present disclosure, the collapsed antechamber includes a stiff, sharpened tip, configured to penetrate tissue.

According to some embodiments of the present disclosure, the discharge electrode extends around at least a portion of a circumference of the gas delivery lumen.

According to some embodiments of the present disclosure, the discharge electrode is positioned with the gas delivery lumen, and surrounded by the flow of ionization gas.

According to some embodiments of the present disclosure, an outer diameter of the plasma delivery tip is less than 5 mm.

According to an aspect of some embodiments of the present disclosure, there is provided a method of operating a plasma delivery tip, including: contaminating an interior of a gas delivery lumen of the plasma delivery tip with liquid; and operating the plasma delivery tip to generate plasma.

According to some embodiments of the present disclosure, the lumen is less than 5 mm in diameter.

According to an aspect of some embodiments of the present disclosure, there is provided a method of operating a plasma delivery tip, including: navigating the plasma delivery tip to an aqueous fluid in contact with a target surface; directing plasma from the plasma delivery tip onto the fluid; and redistributing reactive species induced within the fluid by the plasma to the target surface.

According to some embodiments of the present disclosure, the target surface is inaccessible to plasma directed from the plasma delivery tip.

According to some embodiments of the present disclosure, the redistributing includes supplying fluid that displaces the aqueous fluid.

According to some embodiments of the present disclosure, the redistributing includes agitating the aqueous fluid.

According to some embodiments of the present disclosure, the redistributing includes allowing the aqueous fluid to redistribute to at least partially dried regions of the target surface.

According to some embodiments of the present disclosure, the method includes drying the at least partially dried regions of the target surface.

According to an aspect of some embodiments of the present disclosure, there is provided a plasma delivery tip of a medical grade plasma generating device, including: a gas delivery lumen defined within a circumferential wall having a proximal-to-distal axis and acting as a conduit for a flow of ionizable gas flowing out of an aperture of the gas delivery lumen; and a discharge electrode, positioned to receive pulses of high voltage from an electrical connection with a power supply of the plasma generating device and transmit the pulses into the flow of ionizable gas through a plasma generating region of the gas delivery lumen having a first inner diameter; wherein an inner diameter of the aperture is larger than the first inner diameter.

According to some embodiments of the present disclosure, a distal portion of the circumferential wall distal to the discharge electrode is collapsible.

According to some embodiments of the present disclosure, the circumferential wall includes a thinner-walled section distal to the discharge electrode, and a thicker-walled section within the plasma generating region.

According to some embodiments of the present disclosure, the thinner-walled section and the thicker-walled section are fixed relative to each other along the proximal-to-distal axis.

According to some embodiments of the present disclosure, the thinner-walled section and the thicker-walled section are movable relative to each other along the proximal-to-distal axis through a maximum relative displacement of 50 mm or less.

According to an aspect of some embodiments of the present disclosure, there is provided a method of operating plasma delivery tip, including: navigating the plasma delivery tip to a target, while a closure positioned to prevent contamination of an interior region of the delivery tip extending along a discharge electrode remains closed; opening the closure; and operating the discharge electrode to generate cold plasma.

According to some embodiments of the present disclosure, the closure includes a valve, and opening the valve includes delivering a flow of ionization gas through the plasma delivery tip to press against the valve.

According to some embodiments of the present disclosure, the method includes pressing a distal side of the plasma delivery tip against a target before opening the closure.

According to some embodiments of the present disclosure, opening the closure occurs before the delivering.

According to an aspect of some embodiments of the present disclosure, there is provided a method of operating a plasma delivery tip, including: navigating the plasma delivery tip to a target; pressing a distal side of the plasma delivery tip against a target; expanding a distal portion of the plasma delivery tip; and operating the plasma delivery tip to generate cold plasma.

According to some embodiments of the present disclosure, the expanding includes increasing a pressure within the distal portion while the distal portion seals against the target.

According to an aspect of some embodiments of the present disclosure, there is provided a method of operating a plasma delivery tip within a living body, including: navigating the plasma delivery tip to a position within an intrabody lumen; blowing ionization gas out of a distal aperture of a gas delivery lumen of the plasma delivery tip with liquid during navigation of the plasma delivery tip within the living body; and initiating ionization of the ionization gas within the intrabody lumen, while continuing the blowing.

According to an aspect of some embodiments of the present disclosure, there is provided a medical grade plasma generating device including: a probe, sized for insertion to a selected portion of a body lumen and having a plasma-generating distal tip including a discharge electrode and an aperture through which ionization gas flows; a plurality of balloons through at least one of which the probe extends; the plurality of balloons being sized and positioned to inflate within the selected portion of the body lumen, sealing the aperture between them.

According to some embodiments of the present disclosure, balloons are sized to seal a portion of a vascular lumen.

According to some embodiments of the present disclosure, balloons are sized to seal a portion of an intestinal lumen.

According to an aspect of some embodiments of the present disclosure, there is provided a method of delivering plasma to a selected portion of a liquid-carrying body lumen, the method including: inserting a plasma-delivering aperture of a plasma-generating portion of a plasma delivery device to reach the selected portion of the body lumen; sealing the selected portion distally and proximally to the aperture; removing the liquid from the selected portion; and delivering plasma to the selected portion through the plasma-delivering aperture.

According to some embodiments of the present disclosure, the sealing includes inflating balloons distal and proximal to the aperture.

According to an aspect of some embodiments of the present disclosure, there is provided a method of delivering plasma to an internal body region, the method including: inserting a first and a second probe to the body region; and using the first and second probes: delivering ionization gas, ionizing the gas with a voltage to generate plasma, and scavenging the ionization gas; wherein the first probe is used to perform no more than two of the delivering gas, ionizing gas, and scavenging gas, and the second probe performs at least one of the remaining of the delivering gas, ionizing gas, and scavenging gas.

According to some embodiments of the present disclosure, the first probe is delivered to the body region via a flexible probe navigated through a body cavity, and the second probe is delivered to the body region via a rigid probe inserted percutaneously.

According to some embodiments of the present disclosure, the method also includes delivering a supplemental fluid to the internal body region, the supplemental fluid including a molecular species which reacts with the ionized ionization gas.

According to some embodiments of the present disclosure, at least one of the first and second probes is positioned robotically.

According to an aspect of some embodiments of the present disclosure, there is provided a medical grade plasma generating device including: a probe, sized for insertion to a selected portion of a body lumen and having a plasma-generating distal tip including a discharge electrode and an aperture through which ionization gas flows; a switching valve, positioned on a proximal side of the plasma-generating distal tip, and operable to switch between delivering the ionization gas into a lumen of the probe, and delivering another gas into the lumen of the probe.

According to an aspect of some embodiments of the present disclosure, there is provided a method of generating plasma within a body lumen, the method including: generating plasma from ionization gas flowing to the body lumen through an aperture of a plasma-generating probe; halting the flow of ionization gas; delivering a supplemental fluid to the body lumen through the aperture of the plasma-generating probe; and resuming the generating, while the plasma-generating probe remains in the body lumen.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system" (e.g., a method may be implemented using "computer circuitry"). Furthermore, some embodiments of the present disclosure may take the form of a computer program product embodied in one or more computer readable medium(s) having computer readable program code embodied thereon. Implementation of the method and/or system of some embodiments of the present disclosure can involve performing and/or completing selected tasks manually, automatically, or a combination thereof. Moreover, according to actual instrumentation and equipment of some embodiments of the method and/or system of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In some embodiments of the present disclosure, one or more tasks performed in method and/or by system are performed by a data processor (also referred to herein as a "digital processor", in reference to data processors which operate using groups of digital bits), such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the present disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. A computer readable storage medium may also contain or store information for use by such a program, for example, data structured in the way it is recorded by the computer readable storage medium so that a computer program can access it as, for example, one or more tables, lists, arrays, data trees, and/or another data structure. Herein a computer readable storage medium which records data in a form retrievable as groups of digital bits is also referred to as a digital memory. It should be understood that a computer readable storage medium, in some embodiments, is optionally also used as a computer writable storage medium, in the case of a computer readable storage medium which is not read-only in nature, and/or in a read-only state.

Herein, a data processor is said to be "configured" to perform data processing actions insofar as it is coupled to a computer readable medium to receive instructions and/or data therefrom, process them, and/or store processing results in the same or another computer readable medium. The processing performed (optionally on the data) is specified by the instructions, with the effect that the processor operates according to the instructions. The act of processing may be referred to additionally or alternatively by one or more other terms; for example: comparing, estimating, determining, calculating, identifying, associating, storing, analyzing, selecting, and/or transforming. For example, in some embodiments, a digital processor receives instructions and data from a digital memory, processes the data according to the instructions, and/or stores processing results in the digital memory. In some embodiments, "providing" processing results comprises one or more of transmitting, storing and/or presenting processing results. Presenting optionally comprises showing on a display, indicating by sound, printing on a printout, or otherwise giving results in a form accessible to human sensory capabilities.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the Drawings:

FIG. 2A schematically represents a plasma delivery tip, including an antechamber which provides longitudinal separation between a site of plasma generation near discharge electrode, and an external volume surrounding the plasma delivery tip, according to some embodiments of the present disclosure;

FIGS. 2B-2E schematically represent valved configurations of plasma delivery tips which generate plasma using a flow of ionizing gas flowing along a lumen around which a circumferentially positioned discharge electrode extends, according to some embodiments of the present disclosure;

FIGS. 3A-3F schematically represent valved configurations of plasma delivery tips which generate plasma using a flow of ionizing gas flowing along a lumen within which a discharge electrode is positioned, according to some embodiments of the present disclosure;

FIGS. 4A-4C schematically represent distal-side views of different valve designs, according to some embodiments of the present disclosure;

DESCRIPTION OF SPECIFIC EMBODIMENTS OF THE INVENTION

Figure 1A:
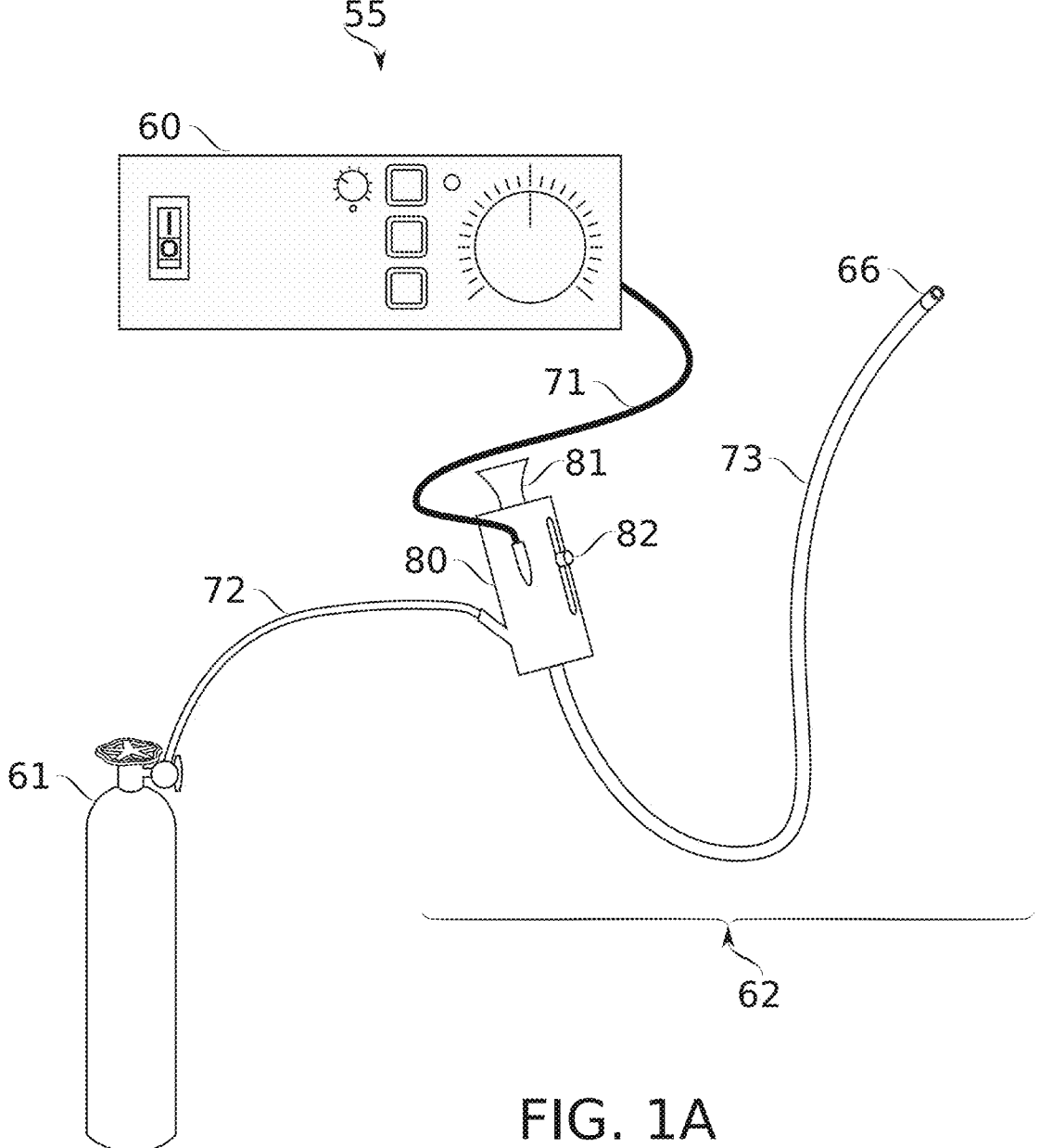
FIGS. 1A-1B schematically represent plasma treatment devices, according to some embodiments of the present disclosure.

The present invention, in some embodiments thereof, relates to the field of cold atmospheric plasma generation and more particularly, to delivery of cold plasma within body cavities.

Overview

An aspect of some embodiments of the present disclosure relates to cold (non-thermal) plasma generating devices configured to resist ingress of contaminants while being navigated within body cavities and/or while being used to delivery plasma to living tissue while in a body cavity. The plasma generating devices are configured to provide cold (non-thermal) plasma to living tissue under conditions of medical-grade temperature, safety, and sterility.

Potentially, the cold plasma has therapeutic effects, e.g., it may act to destroy and/or trigger the destruction of tumor cells and/or pathogens such as viral particles, bacteria, and/or fungi.

Mechanisms of treatment action are an area of ongoing research. A suggested mechanism of action for this involves free radicals (e.g., $OH^-$), for example, oxidative stress caused by free radicals. Treatment potentially exploits differential sensitivity of normal tissue and from a targeted tumor and/or pathogen to free radicals. Treatment effects potentially depend on interactions between parameters of the target (e.g., surrounding fluid, target size, and/or target type) and parameters of the plasma delivered (e.g., generated ionized species, their concentrations and/or ratios). Parameters of the plasma delivered in turn potentially are affected by parameters of the generation of the plasma (e.g., ionization medium composition and/or electrical parameters), and parameters of the plasm plume itself (e.g., geometry, containment, flow, and/or quenching).

Herein, references to "plasma" and "plasma plume" refer more specifically to cold plasma (e.g., plasma at a temperature of 50° C. or less, and preferably delivered at a temperature less than body temperature, e.g., within a range of about 20° C.-30° C.). The cold plasma is generally delivered under conditions of approximately atmospheric pressure, and accordingly also referred to as "cold atmospheric plasma" or CAP.

The tissue target to which cold plasma is delivered, in some embodiments, is internal to a living body. Optionally, the target is outside a living body, and optionally the target is not a portion of a living human body. For example, the target is optionally a calibration target, e.g., a target instrumented to characterize what plasma is produced at different settings of the plasma delivery device, optionally including different parameter settings of the plasma delivery tip; for example: different dielectric barrier thicknesses, different gas delivery lumen diameters, and/or different discharge electrode widths. Additionally or alternatively, the target is an assay target; e.g., a target of an in vitro and/or ex vivo assay of cold plasma effects (e.g., under conditions of different parameter settings of the plasma delivery tip) on one or more types of, for example: tumor cells, pathogen cells, viral particles, healthy cells, and/or tissue samples.

Cold plasma is generated in a non-equilibrium state with respect to its environment, and its ionization state rapidly decays as charged species interact with each other, with other species in the ionization gas, and/or with molecules in the environment.

In some embodiments, a plume of cold plasma (of, e.g., about 1-20 mm in length) is generated from a high-voltage discharge electrode operated within an ionization gas environment created near the target. Characteristic of its non-equilibrium state, cold plasma is low-ionized.

Ionization is estimated, for some cold plasmas, as being (within a factor of about 10) about a part per million and/or $10^{11}$-$10^{13}$ electrons/cm$^3$. The generated plasma is carried on toward the target by flowing of the ionizable gas.

An array of potential problems are associated with contamination of the plasma generation and/or delivery elements of a medical grade cold plasma delivery system.

Body cavities are wet places, with the fluid carrying solutes (e.g., electrolytes and/or macromolecules) and/or suspended particles (e.g., cells and/or fragments thereof).

Some presence of aqueous molecules may be useful for enhancing treatment effects: for example, $OH^-$ free radical generation by plasma may be enhanced when the target itself is wet, and optionally by deliberate introduction of gas-phase $H_2O$ within the ionization gas mix itself. Plasma delivered to a fluid (e.g., an aqueous liquid) may "activate" the fluid, so that ionic and/or molecular species in the fluid itself become more reactive. The fluid itself may then deliver treatment effects to a treatment target, by serving as a medium that allows further redistribution of those reactive species.

However, excess amounts of moisture in the wrong place are potentially inimical to the generation and/or propagation of plasma. For example, if a plasma electron loses energy to generate an $OH^-$ radical where it will not reach the target, it is no longer available to treat the target itself. Moisture potentially interferes with voltage field strengths and/or plugs the gas delivery lumen. This potentially results in weakened and/or less reliable plasma generation.

Moisture (water) can be in liquid or gaseous form. Of particular concern is liquid moisture within the lumenal space of the plasma delivery tip. This can affect electrical field strengths encountered by ionization gas in the region of plasma generation, and/or induce quenching of plasma once it is generated. Liquid that evaporates or is otherwise evacuated can also create a potential problem, since it may contain electrolytes and/or suspended particles which remain behind as a residue that contaminates, quenches, and/or otherwise affects plasma generation and/or delivery.

Gaseous water (e.g., humidity) is liable to being blown out of the way once a flow of ionization gas begins—but gaseous water can also intrude and precipitate to form droplets. For example, cold plasma generated at room temperature may cool water-saturated body temperature gases to a degree sufficient to induce condensation.

Accordingly, it is a potential advantage to construct and operate plasma delivery tips to exclude the intrusion of moisture in liquid and/or gaseous form.

In some embodiments, plasma delivery tip sites of plasma generation and "antechambers" comprising post-generation site compartments with an open distal aperture are small: for example, in a longitudinal range (along a proximal-distal axis) between about 1 mm and 10 mm, and with an outer diameter of about 15 mm or less, about 10 mm or less, about 5 mm or less, about 4 mm or less, or about 3 mm or less. Corresponding inner diameters are smaller; optionally in a range less than 1 mm (e.g., 0.4-0.8 mm, for example), or up to about 3-5 mm in somewhat larger body lumens, or to a range of up to about the diameter of any of the outer diameters listed, minus an overall double-wall thickness of about 0.5-2 mm. Accordingly, a rather small liquid contamination (potentially a microliter of liquid, or even less) may significantly disrupt treatment efficacy at a target site.

In some embodiments, an inner diameter of a plasma delivery tip is furthermore expandable, e.g., by a factor of 1.5×, 2×, 3× or more (e.g., compared to a collapsed diameter of the plasma delivery tip, and optionally compared to a lumenal diameter of the gas deliver tube at the longitudinal position of the discharge electrode). Optionally, the expandable portion of the plasma delivery tip is tapered (and wider at its distal end) when expanded. This potentially increases the target area which is simultaneously treatable by a plasma delivery probe. However, it includes the potential risk of increasing exposure to fluid contamination. Upon re-collapse, intruding fluid may become trapped and/or spread within the plasma delivery tip.

At these dimensions, it should also be noted, wetting and surface tension phenomena are potentially significant considerations in the management of liquid ingress. For example, liquid with a high surface tension (e.g., many aqueous liquids) does not necessarily easily intrude into small apertures except under pressure differentials large enough to overcome surface tension. Contrariwise, wetting (e.g., accompanied by a process of capillary action) could be debilitating if permitted.

In some embodiments, use is made of hydrophobic materials and/or coatings to construct a plasma delivery tip, potentially preventing wetting and/or capillary action and enhancing contamination-excluding properties related to surface tension phenomena. It should be noted, however, that high electrical field conditions (used, e.g., to generate plasma) have some potential to interfere with surface tension phenomena by electrowetting. Plasma itself may also induce surface modifications which affect hydrophobicity.

In some embodiments, contamination exclusion comprises use of the flow of ionization gas itself to fill, pressurize, and/or dry spaces within the plasma generating probe. As long as pressure is maintained, this potentially prevents ingress by low-pressure fluids. In some embodiments, alternative or additional protection against contaminant ingress is provided.

In some embodiments, contamination exclusion comprises a closure (e.g., a sealing member) which is reversibly or irreversibly opened to allow delivery of plasma. In some embodiments, a plasma delivery tip is valved (i.e., the closure comprises a valve), with a valve located between a distal aperture of a plasma delivery tip and the apparatus comprising the discharge electrode at the site where plasma is generated. Optionally, the valve comprises the distal aperture itself. In some embodiments, a closure structure is provided which is positioned distally beyond the distal aperture, e.g., in the form of a "calyx", which, when opened, exposes the distal aperture behind and/or underneath it. In some embodiments, a portion of the plasma delivery tip is interchangeable between collapsed and expanded configurations, wherein the collapsed configuration resists or prevents the intrusion of contamination.

Blocking structures such as these provide potential advantages in situations such as:

Transient high pressure; e.g., upon encountering an obstacle during navigation, which might tend to force contamination back into the tip.

Risk of ingress by solid particles—this may occur even when pressure is high; for example, if flow itself is low.

Tight size constraints. The potential to inflate a small space may create a risk of tissue damage such as tearing. Limits on the lumenal cross-section of devices that can be introduced to a such a space may prevent the introduction of a gas scavenging lumen to counteract inflation.

Even with simultaneous gas scavenging, not all intrabody lumenal spaces are necessarily suitable for continuous perfusion with gas; e.g., due to risk of embolism or tissue damage.

Herein, "scavenging" gas means to evacuate the gas through a conduit dedicated to such evacuation after the gas has performed an initial function; e.g., participated in the generation of plasma plume, opening of a valve, and/or drying or moistening a lumenal wall.

In some embodiments, actuation (e.g., to open a valve or to inflate/expand a structure) is performed using pressure from flow of the ionization gas itself. In some embodiments, actuation is controlled separately, e.g., using mechanical actuators, piezoelectric effects, or another active actuation method. Optionally, control is performed separately but coordinately, e.g., a piezoelectrically actuated valve is opened in coordination with ionization gas delivery. Coordination may be performed in an "open loop" fashion (e.g., by sending commands at coordinate times), and/or by using sensing (e.g., of pressure buildup and/or pressure loss).

Optionally, structures which valve and/or close a distal aperture of a plasma delivery tip are provided in combination, e.g., a calyx (distally beyond the distal aperture of the gas delivery lumen) and a valve (proximal to the aperture) are optionally provided together.

Optionally, structures which valve and/or close a distal aperture of a plasma delivery tip have auxiliary functions. For example, a distal end of the plasma delivery tip may be soft and/or blunt so that it acts as an atraumatic tip (e.g., at least partially collapses, deflects, and/or deforms upon exertion of sufficient pressure. Alternatively, in some embodiments, a distal end of the plasma delivery tip may be stiff and/or sharpened so that it can dissect and/or penetrate tissue. For example, the plasma delivery tip's distal end is optionally beveled to provide a trocar-like tip. In some embodiments, the distal end of the plasma delivery tip (when closed) is gathered to a sharpened point configured to penetrate tissue, e.g., like a needle.

A complementary approach to managing contaminants by exclusion is to scavenge moisture from a working area in order to remove aqueous molecules and/or control their concentration. In some embodiments, a plasma delivery tip is provided with a gas scavenging lumen which is optionally operable to remove ionization gas as it is delivered. While gas scavenging is performed to remove gas from an antechamber positioned apposite to a target surface, this potentially helps to dry and/or equilibrate (e.g., in coordination with aqueous species delivered within the ionizing gas) the level of moisture on the target surface and/or surfaces inside the antechamber itself. This potentially assists with activated fluid redistribution of reactive species to surfaces of a treatment target. For example, an overly dry or an overly wet target surface may absorb and/or generate reactive species differently (e.g., less efficiently) than an intermediately moistened target surface. Optionally, a target surface is dried of environmental liquid, and then moistened by activated fluid. Potentially, initial surface drying promotes the redistribution of activated fluid, e.g., by promoting fluid migration due to wetting surface interactions.

Optionally, purging of contamination, moisture and fluids is performed by reversing a direction of flow in the gas delivery lumen which normally operates to provide ionization gas from a source. Optionally the gas delivery lumen alternates between generating plasma and performing suction. In embodiments comprising a valve, the valve is optionally forced open by means other than internal pressure. To avoid sucking in new contamination, a supply of clean gas is optionally provided to a distal end of the plasma delivery tip (e.g., via another lumen of the plasma treatment device; for example, scavenging lumen which is alternatively used as an evacuation conduit for waste ionization gas). The supply can be in a surplus to the suction. In embodiments comprising a valve, the supply can be provided through an aperture located proximal to the valve, so that the valve can remain shut, or if it opens, it is opened together with a pressure which resists further ingress of contamination. Accordingly, in some embodiments, a valve is placed where it protects a plurality of lumens from contamination when closed.

In some embodiments, a plasma delivery tip is allowed to become at least partially contaminated (e.g., by liquid) within an interior of the plasma delivery tip, and then operated to generate plasma within a body lumen. Optionally, the contamination is purged (e.g., by a flow of gas) before plasma generation begins. Optionally, the contamination is confined to an interior portion of the plasma delivery tip which is sealed off from functionally sensitive areas (e.g., a plasma generation site) by a valve or other barrier. In some embodiments, an interior diameter of the plasma delivery tip is less than 5 mm, less than 3 mm, or less than 1 mm; e.g., of a size which is small enough that even slight contamination (e.g., by a droplet of liquid, and optionally even a droplet of liquid condensing from gas within the body lumen) is liable to significantly impair plasma generation.

An aspect of some embodiments of the preset disclosure relates to the use of plasma-activated fluid to distribute reactive species within a body lumen.

In some embodiments, plasma activated fluid (e.g., aqueous liquid) is used to help distribute therapeutic effects of plasma to a larger region than may receive direct contact from a plasma plume. This is a potential advantage for increasing a quantity of surface area treated (e.g., compared to surface area impinged on directly by the plasma plume), and/or for allowing reactive species to reach surfaces which are otherwise inaccessible to direct treatment with a plasma plume.

Electrons and/or ionized species in a plasma plume potentially enter surrounding fluids and/or interact with species in fluids contacted by the plasma plume to "activate" the fluid. The activated fluid then comprises reactive (and potentially relatively short-lived) species, which may be capable of readily modifying molecules with which they come into contact, including cellular molecules. Accordingly, activated fluid may propagate therapeutic effects induced by the plasma. There is, accordingly, a potential advantage in using fluid-based redistribution of plasma effects through the use of plasma-activated fluid (gas and/or liquid).

Being short-lived, the most reactive species in a plasma-activated fluid will tend to quickly decay in concentration after their initial formation. There is a potential advantage in activating the plasma-activated fluid at the site of treatment, to reduce transport delays during which potential therapeutic effects weaken due to the loss of reactive species.

Moreover, there is a potential advantage to controlling the movements and/or geometry of the activated fluid that distributes active species. For example, fluid in the form of a thin liquid layer provides potentially a shorter and/or more constrained path to reach a target. Fluid which is spreading (e.g., under pressure and/or by surface interactions) from a site of introduction potentially carries along with it reactive species, allowing them to spread faster than they would distribute, e.g., by diffusion.

Herein the term "activated fluid" refers to fluids (however introduced) which encounter the plasma plume away from the region of plasma plume formation. These fluids may comprise gas and/or liquid. The fluids optionally include gaseous phase species which condense to liquid phase, and/or liquid phase species which evaporate to gaseous phase. Before activation, these fluids are referred to herein as "environmental" fluids. The environmental fluids may comprise fluids pre-existing and/or naturally introduced to regions near the target (e.g., body fluids, inspired atmospheric gases, and the like). Additionally or alternatively, environmental fluids comprise fluids artificially introduced near the target. Optionally, artificial introduction is by a lumen separate from the gas delivery lumen. For example, any of the gas scavenging lumens described herein is optionally or additionally operated as a lumen for the introduction of fluid. Fluids introduced by the gas delivery lumen itself are herein considered originally as "part of the plasma plume" if plasma is being generated as they reach the site of plasma generation. However, the gas delivery lumen can also deliver environmental fluids. For example, during times without plasma generation, the ionization gas (or another fluid) is optionally exhausted into the surrounding environment where it becomes a medium of environmental fluid which may later be activated. "Spent" or "waste" ionization gas (even if originally emitted part of the plasma plume itself) may optionally become re-activated by a re-encounter with the current plasma plume, and thus serve also as "environmental" fluid.

Activated gaseous fluids have the potential advantage of creating a rapid and/or wide distribution of reactive species; however, gaseous fluids also tend to associate with a relatively high ratio of volume-to-surface area (unless this ratio constrained by a shape of the space bounding the gaseous fluids). Activated liquid fluids (e.g., aqueous liquids) have the potential advantage of spreading over surfaces as a film, reducing the volume-to-surface ratio. This potentially results in more efficient transfer of reactive species through target surfaces.

There may also be a kinetic advantage for the repartitioning of reactive species in aqueous fluids into semi-aqueous targets like cellular tissue, compared to the kinetics of direct condensation from the gaseous phase. For example, the disruption and/or mixing imparted by "jetting" gaseous plasma into a liquid potentially speeds the kinetics of initial condensation/production of reactive species to/within the liquid, after which the activated liquid serves as a medium for redistributing reactive species across a target's surface.

An aspect of some embodiments of the present disclosure relates to the supply of supplementary atomic and/or molecular species in alternation with a primary ionization gas. In some embodiments, targeted effects of plasma on a treated target involve molecular species (referred to herein as supplementary species) which are not found in the ionization gas which has been selected for generating the plasma itself. For example, the ionization gas may comprise a composition of helium, neon, and/or argon, but plasma-mediated effects may involve ions of other molecular species, generated, for example, from oxygen, nitrogen, carbon dioxide, argon, and/or water. In the case of plasma treatments applied to surfaces exposed to open atmosphere, the molecular reagents from which these ionic species are generate will generally be available from atmospheric molecules. In an enclosed space such as a body lumen interior, however, these reagents may not be present, or may be used up before treatment is complete. Supplying these reagents along with the ionization gas, however, may have the effect of altering (raising) the breakdown threshold voltage of the gas. This potentially terminates plasma generation; and/or necessitates raising the supplied voltage to levels beyond those which may be optimal from other considerations such as rate of power dissipation and/or voltage withstanding capacity of the device components overall.

In some embodiments of the present disclosure, the supplementary species are supplied in periodic alternation with ionization gas; for example a period of about 20 seconds for every 1-5 second gas supplying supplementary species. The duty cycle of ionization gas delivery may be, for example, between about 70%-99% of the time. Remaining time in the duty cycle is used to supply supplementary molecular species. In some embodiments, the valve is actuated by a controller which also sets the timing and duty cycle of the valve's operation.

In some embodiments, the cycle time of a duty cycle switching between a fluid carrying supplementary species and a ionization gas is shortened from several seconds full-cycle to about one second, or even shorter, for example, every 500 msec, 200 msec, or 100 msec. Optionally, the duty cycle is short enough that two or more boluses of at least one of the different fluid compositions is present in a lumen leading to the plasma delivery tip at the same time as one or more boluses of a different fluid composition. Apart from potential mixing at their boundaries, central regions of the different boluses remain unmixed, at least until after their discharge past the discharge electrode and/or into the environment. Shortening the cycling time has the potential advantage of improving the homogenization of ionization gas with supplementary species, and/or reducing the intervals between adjustment of fluid/gas inputs to the system to balance relative amounts of ionization gas and supplementary species. Optionally, homogenization is assisted by the use of baffles.

In some embodiments, control of the delivery of electrical power is exercised to coincide with the passage of a bolus of ionization gas past a discharge electrode, and to be switched off when other fluid is passing the discharge electrode. This may be performed, in some embodiments, by placing control of switching as well as electrical outputs under the command of a single controller; or by having a plurality of controllers operating in communication with each other and/or with a common set of operating parameters; e.g., parameters stored in a computer memory, and/or set by the electrical value of a control such as a variable resistor.

In some embodiments of the present disclosure, alternation of fluids comprises delivery of a liquid such as saline through the ionization gas delivery lumen. The switch back to ionization gas is optionally accompanied and/or preceded by delivery of a drying gas through the gas delivery lumen to assist in purging the liquid. Injection of liquid through the ionization gas delivery lumen may be performed as a way of cleaning the lumen, and/or as a way of helping to ensure that there is no backflow into the lumen. Liquid fluid used for cleaning and/or maintaining cleanliness is optionally injected at selected times (rather than cyclically), or with any suitable cyclic interval, for example as described for the general case of alternating fluid injection.

In some embodiments, gas delivering supplementary species also acts to ensure that gas being exhausted from the region of plasma application itself has too high a breakdown threshold to be inadvertently converted to plasma. This may be significant, for example, when gas is scavenged using a lumen of a probe which runs alongside an electrical conductor used to generate plasma at the probe's tip. In some embodiments, supplementary gas is supplied often enough and in sufficient amounts to maintain a sufficient margin of breakdown voltage above the voltage being carried by a conductor positioned near a gas exhaust conduit.

An aspect of some embodiments of the present disclosure relates to the delivery of plasma to a normally or potentially liquid-filled lumenal space such as a blood vessel, gastrointestinal tract segment, or urinary tract segment. Full immersion in aqueous liquid is generally incompatible with the generation of plasma. Accordingly, in order to bring plasma to regions within liquid-filled body lumens such as blood vessels, it is a potential advantage to provide systems which are capable of establishing an volume within the body lumen isolated from fluid communication with adjacent volumes, empty it, perform plasma treatment, and then, if necessary, refill the isolated area with liquid (remove gas bubbles which may potentially lead to embolism) the isolated volume is released again.

In some embodiments, plasma delivery tips are provided with deployable structures such as balloons which can reversibly establish a fluid seal with a body lumen by inflating or otherwise deploying to establish fluid isolation, and then deflating after treatment is completed.

Evacuation of the area isolated for treatment is accomplished, in some embodiments, by pushing gas into the area while allowing existing fluid to drain out in response. Optionally, drainage is assisted by suction pressure. Optionally, a washing liquid is used as part of the evacuation procedure, for example, to replace viscous liquid such as blood with a less viscous liquid such as saline, followed by the introduction of gas to allow plasma generation. The gas may be a dried gas, which potentially also assists in removing liquid from the isolated volume.

Generally, the system used to isolate the area for treatment comprises a distal sealing element and a proximal sealing element, between which is an aperture through which plasma and/or ionization gas is introduced. The two sealing elements may both be integral parts of the plasma delivery tip itself; or one or both of them may be separately introduced and positioned.

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Plasma Treatment Devices

Figure 1B:
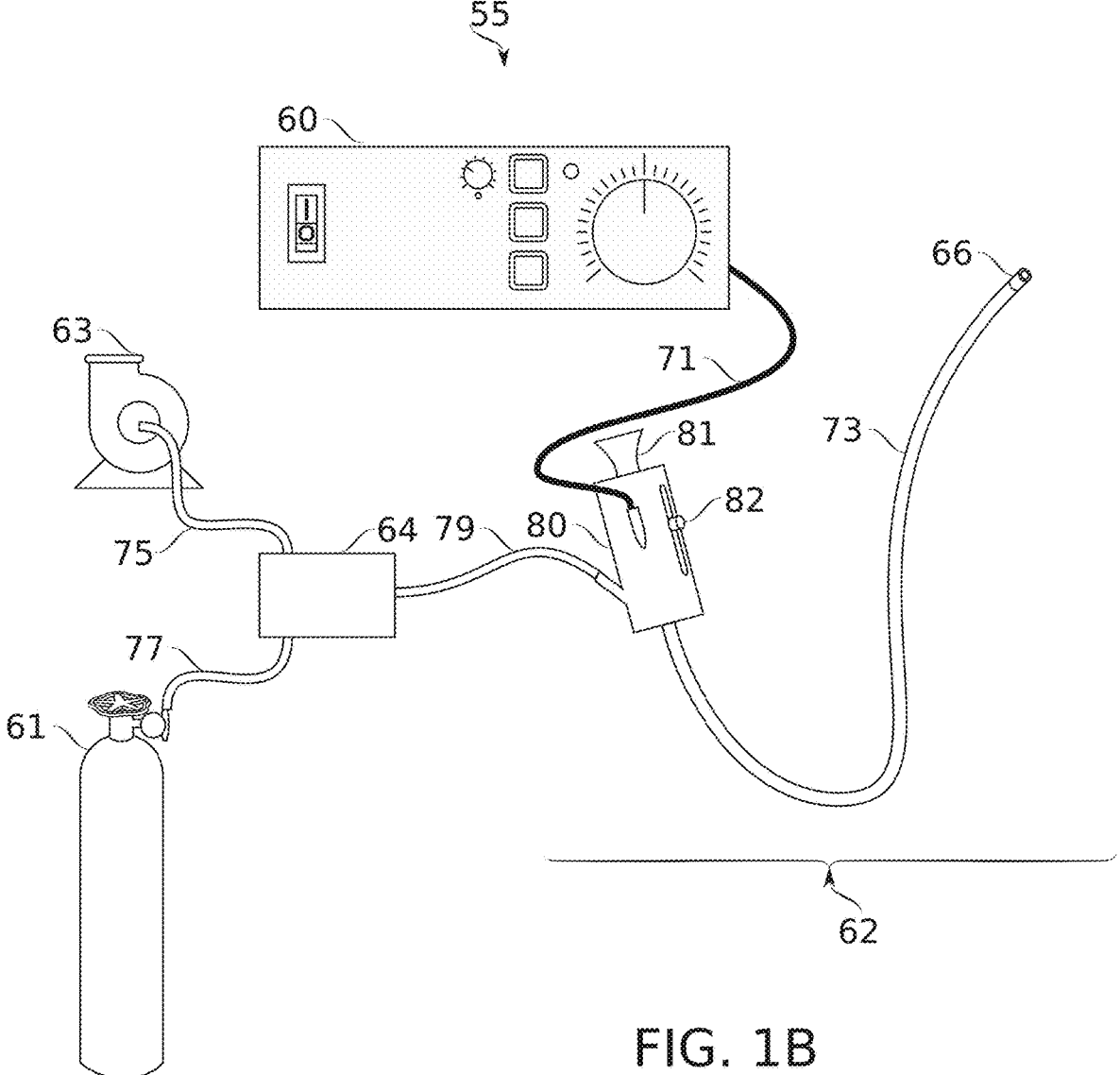

Reference is now made to FIGS. 1A-1B, which schematically represent configurations of plasma treatment devices 55 according to some embodiments of the present disclosure.

Plasma treatment device 55, in some embodiments, comprises a high voltage power controller 60 and an ionization gas supply 61 interconnected to a plasma probe assembly 62. High voltage power controller 60 supplies ionizing voltage to plasma probe assembly 62 via cable 71 (which may be, for example, a coaxial cable, or another electrical conduit with controlled impedance and shielding along its length). Ionizing gas supply 61 supplies an ionizable gas to plasma probe assembly 62 via tubing 72. The supplied gas may comprise, for example, one or more noble gases such as neon, argon, or helium; and/or other gas(es) suitable for ionization into a plasma plume. Optionally, cable 71 and tubing 72 are integrated into a single cabling unit which connects with plasma probe assembly 62. Optionally, high voltage power controller 60 and ionization gas supply 61 are integrally housed.

Plasma probe assembly 62, optionally comprises a handle 80. Handle 80 is optionally provided with controls 81, 82 for controlling actuation of probe conduit 73 and/or plasma delivery tip 66, for controlling functions of power controller 60, and/or for controlling ionizable gas delivery from gas supply 61. Optionally, plasma probe assembly 62 physically integrates power functions and gas delivery functions into probe conduit without use of a dedicated handle. In some embodiments, probe conduit 73 includes both a lumen for delivery of ionization gas, and high voltage (e.g., a continuation of cable 71 and tubing 72).

In some embodiments of the present invention, probe conduit 73 and plasma delivery tip 66 are sized and otherwise configured (e.g., safety-configured) for the delivery of cold plasma to an intrabody location. In some embodiments of the present disclosure, plasma delivery tips are configured to be navigable into intrabody target regions through lumens and/or apertures of, for example: about 15 mm or less, about 10 mm or less, about 5 mm or less, about 4 mm or less, or about 3 mm or less. A diameter of a gas delivery lumen delivering ionization gas to be ionized to plasma at the plasma delivery tip, and/or delivering the ionized gas itself as a plasma plume leaving the plasma delivery tip optionally ranges between about 0.4 mm and 8 mm. The portion of the plasma delivery tip which generates and shapes the plasma plume is optionally between about 4 mm-30 mm in length. Longer lengths are optionally used with correspondingly higher discharge voltages, to prevent dielectric breakdown.

FIG. 1A illustrates a plasma probe assembly 62 in a "stand alone" configuration, for example a configuration which may be itself used as a navigable catheter to reach an intrabody target. However, it should be understood that, in some embodiments, a plasma probe assembly 62 is optionally used together with another device; for example, by passing it through the working channel of an endoscope, or by inserting it through the lumen of a separate catheter. Plasma probe assembly 62 is illustrated as comprising a flexible probe conduit 73, however, it should be understood that probe conduit 73 is optionally stiff, and optionally straight or curved. Probe conduit 73 is optionally of any suitable length to reach its target.

Some embodiments of the present disclosure are described as comprising a sheath or overtube with a lumen within which elements of a plasma delivery tip advance. Optionally, the sheath is a part of probe conduit 73. Optionally, the sheath is provided as the lumen of a device to which the plasma probe assembly is inserted, for example, a working channel of an endoscope or a separately provided catheter. Embodiments shown and/or described without a sheath are optionally provided and/or operated with one. Conversely, embodiments described with a sheath are optionally provided and/or operated "sheath less", albeit that features specifically reliant on the sheath (e.g., using a portion of its lumenal space as a gas and/or plasma return pathway) may then be unavailable.

Power delivery to the plasma plume through a plasma delivery tip 66 is optionally in the range of about 0.1-10 W, 0.1-5 W, or 1-2 W (e.g., about 1.5 W). Current delivery through a plasma deliver tip is optionally in the range of about 5-20 mA (e.g., about 8 mA). Voltage supplied to generate plasma is optionally in the range of about 750-850 V (at a radfrequency). Optionally, the voltage is higher, e.g., up to about 1000 V or 1600 V. Ionization flow rate (at about atmospheric pressure) through a plasma delivery tip 66 is optionally within a range between about 0.1 L/min and about 9 L/min, e.g., 0.5 L/min, 2 L/min, 3 L/min, 6 L/min, 9 L/min, or another gas flow rate. Pulse repetition rate (that is, pulses comprising several radfrequency voltage oscillations) is optionally selected from within a range of, e.g., about 100-600 Hz, or about 200-500 Hz. The pulses are optionally in the range of about 100 μsec-1000 μsec; e.g., about 400 μsec, 600 μsec, or another pulse length.

Optionally (FIG. 1B), plasma treatment device 55 comprises a secondary fluid supply 63, which may be a source of clean pressurized air, or another gas composition e.g., oxygen and nitrogen in a non-atmospheric ratio. The provided gas composition optionally comprises other species such as water vapor, and optionally the fluid is in liquid form: saline or water, for example.

Although secondary fluid supply 63 may supply a second ionization gas (e.g., an alternative ionization mixture to the one supplied by ionization gas supply 61), it is a particular feature of some embodiments of the present disclosure that the composition supplied by secondary fluid supply 63 is not itself an ionization gas for plasma treatment device 55; that is, it is not in its unmixed form suitable for ionization by plasma delivery tip 66 (e.g., its ionization energy is too high). However, this composition may contain species which partially ionize or otherwise react in the presence of plasma. In some embodiments, species that are products of these secondary reactions are potentially involved in treatment effects resulting from plasma exposure. Delivery of gas from secondary fluid supply 63 may be, for example, as described for the flow of ionization gas; e.g., a flow rate in a range between about 0.1 L/min and about 10 L/min. Liquids may be delivered in a lower rate, e.g., 0.01 L/min to 0.1 L/min, or another rate of liquid delivery. Gas and liquid deliver may themselves be alternated. In general, secondary fluid supply 63 may itself comprise a plurality of fluid supply sources which can be mixed and/or alternately selected for delivery.

In the schematic representation, secondary fluid supply 63 is represented as a pump, but it may be provided from another pressurized source such as a tank. Provided fluids are optionally filtered, e.g., filtered to remove biological contaminants. The secondary fluid supply 63 itself is optionally provided as part of a plasma treatment device 55; optionally plasma treatment device is configured to receive (e.g., via tube 75) secondary fluid from an externally provided source such as a hospital building's compressed air distribution system.

In some embodiments, tubing 72 (FIG. 1A) is replaced by a plurality of tubes 75, 77, 79 (FIG. 1B). Switching valve 64, in some embodiments, operates to alternate gas delivered through tube 79 to handle 80 from tube 77 (connected to ionization gas supply 61) or tube 75 (connected to secondary gas supply 63).

A potential advantage of this arrangement is that it allows periodic injections of molecular species which, although not needed for the original generation of plasma (or even interfering with such generation), may nonetheless mediate treatment effects. Herein, these species are referred to as "supplementary species". In particular, plasma treatment effects validated by testing performed in open atmosphere conditions are potentially altered (even for the same plasma generating parameters) when plasma is delivered into a confined space such as a body lumen. Even if some level of a gas such as nitrogen or oxygen is originally present, this may be used up or replaced (e.g., by the ionization gas) as plasma generation proceeds. This can apply to environmental molecular species, or to molecular species in the treatment target itself.

More particularly, alternating between the two sources has the potential advantage of introducing the supplementary species into the lumenal space without the need to change the mixture of ionization gas used as the primary medium for plasma generation. For example, the ionization gas from gas supply 61 may be provided for about 20 seconds for every 1-5 second of gas from secondary gas supply 63 (duty cycle of between 20:1 and 4:1). In some embodiments, another ratio used; e.g., a ratio between about 5:1 and 60:1, such as 10:1, 30:1, or 60:1. In some embodiments, the duty cycle is between about 7:3 (70% ionization gas delivery phase) and 99:1 (99% ionization gas delivery phase). The duty cycle is optionally set according to another measurement unit such as volume at atmospheric pressure.

A potential advantage of using unmixed ionization gas from ionization gas supply 61 is that the ionizing energy can remain low, e.g., the voltage can remain within 30% of the threshold voltage for reliable ionization of the unmixed ionization gas. This is a potential advantage in turn for electrical and/or thermal safety, and/or the ability to maintain a small device cross-section (e.g., 7 mm diameter or less; wiring and insulation widths are themselves dependent on power and voltage requirements). If the device is operated near the breakdown threshold, there may be no or insufficiently reliable ionization once even a small proportion of supplementary species gas is introduced, so that it becomes preferable to stop the delivery of ionization gas altogether to allow a higher rate of delivery of the supplementary species, and a shorter interruption in time duration of plasma generation.

Moreover, in some embodiments, spectral characteristics of the plasma are monitored in order to control plasma generation and/or verify that plasma is being delivered as planned. Mixing ionization gas with the supplementary species may complicate this monitoring, e.g., by adding spectral lines that confuse monitoring measurements.

Nevertheless, switching valve 64 can be controlled, in some embodiments, to optionally allow partial mixing of gas from the two gas supply sources 61, 63 during the supplementary species delivery phase. This may allow plasma generation to continue under sub-optimal conditions (e.g., elevated operation voltage and/or uncertain operating results) rather than interrupting it completely. Another potential use of partial mixing is in confirming (based on what percent mixing quenches plasma generation) how far above threshold breakdown voltage the device is actually operating, without having to adjust the voltage itself.

The duty cycle frequency, in some embodiments, is set so that the plasma delivery phase is longer than 10 seconds, e.g., 20 seconds, 30 seconds, or another time. The supplementary species delivery phase is optionally between about 0.5-10 seconds. A longer uninterrupted plasma delivery phase of the duty cycle may make it easier to track where plasma has actually been delivered to, and/or may help keep the plasma plume itself stable. Too long, however, and the supplementary species may become depleted. The duty cycle may, accordingly, be adjusted according to the estimated or observed (e.g., spectrally observed) depletion rate of the supplementary species.

Reference is now made to FIG. 2A, which schematically represents a plasma delivery tip 66, including an antechamber 20 which provides longitudinal separation between a site of plasma generation near discharge electrode 106, and an external volume 11 surrounding the plasma delivery tip 66, according to some embodiments of the present disclosure.

FIG. 2A provides a general schematic of a plasma delivery tip 66 with an antechamber 20. Circumferential wall 101A defines the antechamber 20. Antechamber 20 opens distally into external volume 11, and terminates proximally with the plasma generating region 12 of the plasma delivery tip 66, including a circumferential wall 102A and electrode 106 which together define some important electrical and geometrical properties that affect generation of plasma plume 10. These properties include (1) the inner diameter of circumferential wall 102A, (2) the breakdown voltage of the dielectric barrier which separates electrode 106 from the lumen 95 of circumferential wall 102A, and (3) the proximal-to-distal length of electrode 106, which affects the output voltage of the plasma. Voltage is supplied to discharge electrode 106 along electrical conduit 105, which is optionally a coaxial cable.

In some embodiments, circumferential wall 101A surrounds a lumenal space (the antechamber 20) which is larger in diameter than the space surrounded by circumferential wall 102A. In some embodiments, distal aperture 21 of circumferential wall 101A is positioned at a fixed longitudinal distance from the end of circumferential wall 102A (so long as circumferential wall 101A remains uncollapsed), or at a longitudinal distance which is adjustable only within a short range (e.g., a range of 50 mm or less, 20 mm or less, 10 mm or less, 5 mm or less, or 1 mm or less). A longitudinal length of antechamber 20 is thereby fixed or short-range adjustable accordingly. This distinguishes circumferential wall 101A from, e.g., an overtube along which plasma generating region 12 could be advanced or retracted to any distance. Potential advantages of a fixed-length or short-range adjustable-length antechamber 20 include preventing advance of plasma generating region 12 past aperture 21 (potentially exposing it more directly to fluid contamination), and maintaining more certainty that plasma plume 10 is being generated within its range so that it can reach aperture 21 (and a plasma treatment target optionally positioned thereat).

There is also a potential advantage for allowing a larger area of treatment target to be selected for treatment with the plasma plume 10. For example, when distal aperture 21 is pressed up against a treatment target, the play of plasma plume 10 potentially expands to encompass a larger area at the same time than would be available if there was no inner lumen expansion. At the same time, there is allowed partial decoupling of geometrical parameters governing plasma generation (in plasma generating region 12) from the diameter of antechamber 20. A ratio the thickness of circumferential wall 101A to circumferential wall 102A (i.e., within plasma generating region 12) is optionally 1:2, 1:3, 1:4 or greater. The ratio of wall thicknesses is optionally inverted, e.g., 2:1, 3:1, 4:1 or lesser, which, with a constant outer diameter, results in a narrower outlet, potentially increasing jetting velocity of the plasma plume 10. This potentially increases mixing of plasma plume 10 with surrounding environmental fluid; this is a potential advantage, e.g., for increasing the efficiency of fluid activation.

Circumferential wall 101A is optionally "blunt" or "sharp" (compare, e.g., the embodiments of FIGS. 2B and 2C). Optionally, resistance to collapse of circumferential wall 1010A is selected according to anticipated conditions. A more resistant circumferential wall 1010A is potentially useful, e.g., as a trocar for penetrating tissue, e.g., it is optionally constructed of metal (optionally polymer coated), or a stiff polymer.

A more yielding circumferential wall 1010A is potentially useful, e.g., as an atraumatic tip for navigating within the confines of a delicate body lumen. Circumferential wall 101A is optionally configured as an elastically deformable membrane having a thickness of less than 1000 μm; e.g., about 500 μm, 250 μm, about 100 μm, or another thickness. Optionally, circumferential wall 101A is constructed of a material which, at the chosen thickness, is soft and easily deformed elastically, e.g., it collapses upon exertion of an external pressure less than about 2 bar, 1 bar, 0.5 bar, 0.25 bar, 0.1 bar, 0.05 bar, or another pressure. During plasma delivery, internal pressure exerted by flowing discharging gas helps circumferential wall 101A resist collapse, e.g., when pressed to a target. Thicker circumferential wall 102A provides support from a proximal side.

Figure 3A:
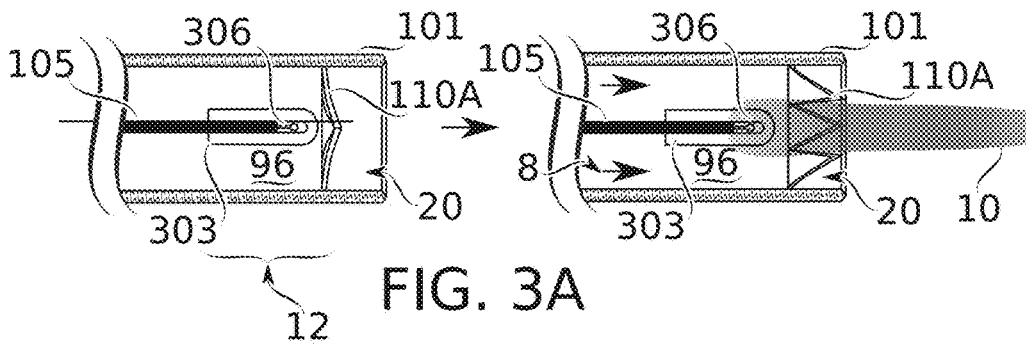

The plasma plume 10 is also optionally affected by adjustments to the orientation and symmetry of components in the plasma generating region 12. The configuration of FIG. 2A is generically representative of arrangements such as FIGS. 2B-2E, wherein plasma is generated using a flow of ionization gas 8 flowing along a lumen 95 defined by a circumferential wall (the wall and/or tube of the lumen 95) around which a circumferentially positioned discharge electrode 106 extends, at least partially around the circumference of lumen 95. It should be understood that a pressure-maintained antechamber 20 is optionally provided to other arrangements; for example, arrangements using a discharge electrode surrounded by a flow of ionization gas, such as illustrated in FIG. 3A (without the valve).

In some embodiments, plasma delivery tip 66 is configured for delivery of plasma to targets within an environment 11 which comprises aqueous molecules, water-saturated gases, and/or free liquid, and potentially are even liquid immersed. However, contamination (e.g., aqueous contamination), can very quickly quench a plasma plume, preventing its effective delivery to the target. Even if the plasma plume is not entirely quenched, the parameters of plasma generation may be changed unpredictably by contamination.

In some embodiments, contamination is prevented by keeping a constant positive pressure of ionization gas 8 within the inner lumens of the plasma delivery tip 66 (that is, constantly "blowing" ionization gas out of a distal aperture of the tip), preventing contaminant ingress to antechamber 20. For plasma delivery, distal aperture 21 of antechamber 20 is optionally pressed up against a target, and/or inserted to a lumenal space that can be cleared of obstructing contaminant, e.g., in part or in whole by gas pressure exerted by the flow of ionization gas 8. For small-lumen devices (e.g., devices with a lumenal diameter of 5 mm or less), the amount of gas which is vented while maintaining positive pressure is potentially low enough that the problem of inflation is negligible; or if not, a portion of the blown gas is optionally scavenged by a return lumen.

It is noted that this method of preventing back-flow of liquid into antechamber 20 and/or plasma generating region 12 has the potential disadvantage of generating continuous gas flow within body lumens through which plasma delivery tip 66 moves, which may not always be acceptable. For example, gas scavenging from within the lumen of plasma delivery tip 66 may not always be available to control pressure build-up. There also potentially remains a risk of liquid contamination should back-pressure ever overcome the forward pressure of the gas, e.g., if the plasma delivery tip enters a particularly confined space. Furthermore, it is a potential advantage to be remain free to fully shut down ionization gas flow on command, for example, to remove disturbance caused by continuous gas flow (e.g., bubbling) which could interfere with imaging and/or procedure monitoring.

Reference is now made to FIGS. 2B-2E, which schematically represent valved configurations of plasma delivery tips which generate plasma using a flow of ionization gas 8 flowing along a lumen around which a circumferentially positioned discharge electrode 106 extends, according to some embodiments of the present disclosure. FIGS. 2B-2C show both closed (left panel) and open (right panel) configurations of a same respective embodiment.

In FIGS. 2B-2C, the wall of antechamber 20 is indicated by circumferential wall 101. In FIG. 2D, antechamber 20 is defined within circumferential wall 101A, distinct, e.g., from a scavenging lumen 96. In FIG. 2E, antechamber 20 is defined by circumferential wall 101 (e.g., if extended beyond circumferential wall 101B), and or by circumferential wall 101B. Corresponding to elements in the plasma generating region 12 of FIG. 2A, is a cutaway view of an electrode 106 implemented as a wire coil, a dielectric barrier layer 103 (which determines the breakdown voltage), and another insulating layer 102 which provides mechanical support and/or electrical insulation from the outside to electrical conduit 105, and electrode 106. Optionally, these different layers are assembled together from separate components (e.g., of separate materials), or integrally formed (e.g., as shown in FIG. 2A). The different layers may be fixedly attached to each other, or they may be movable (e.g., slidable longitudinally and/or rotatable).

In FIG. 2B, a unidirectional (one-way) valve 110A is positioned within antechamber 20. When there is no flow of ionization gas 8 in gas delivery lumen 95, valve 110A remains closed. During plasma generation, valve 110A opens to allow plasma plume 10 to project forward.

Valve 110A is represented in the drawing more specifically by a leaflet valve 110A, but it should be understood that other valve designs are optionally substituted, for this; for example, valve designs as described herein. A commonality of many such valve designs is that they leave a sufficient clear aperture for plasma plume 10 to pass through when they are open, however, the valve may also be used to restrict and/or redirect the plasma plume, for example as discussed in relation to FIG. 3F. Optionally, valve 110A is positioned so that it remains fully within antechamber 20 when open. This allows aperture 21 to optionally be pushed fully up against a target without interference from the valve.

Valve 110A is optionally actuated to open by pressure of ionization gas 8 delivered from a proximal side of the valve 110A. Being a one-way valve, pressure from the distal side does not open valve 110A, allowing it to act as a barrier to liquid ingress. Optionally, valve 110A is actuated independently of gas pressure, for example as described in relation to valve 110D (FIG. 3E). Optionally, lateral vent holes 113 are provided in the wall of antechamber 20, allowing the escape of ionization gas even if distal aperture 21 is blocked (e.g., by being pressed up against tissue to be treated). In some embodiments, this prevents buildup of back-pressure from closing or partially-close valve 110A. Additionally or alternatively to apertures 113, the distal circumference of distal aperture may be configured with notches that provide an escape path for gas. This also provided a potential advantage for keeping pressure near electrode 106 more constant, e.g., avoiding cycles of pressure buildup and release as temporary blockage occurs and is overcome.

In FIG. 2C, antechamber 20 is formed with a trocar tip (that is, a slanted tip, defined by an obliquely angled distal aperture 104). Optionally, the slanted tip assists in penetrating obstacles, for example, membranes or narrow passages. The slanted tip also potentially provides a natural vent for ionization gas in most configurations. Potentially it retains enough gas long enough (particularly if embedded in soft tissue) that liquid can be kept clear of plasma plume 10 until it reaches a tissue surface targeted for treatment.

In some embodiments, ionization gas is allowed to dissipate (e.g., through a natural or artificial body orifice). Optionally, ionization gas is actively scavenged, for example through a channel separate from probe conduit 73, and/or through a channel integrated into probe conduit 73.

FIGS. 2D-2E each add a gas scavenging lumen 96, 97 to the general configuration of FIG. 2B, allowing a return flow 9 of ionization gas and/or liquid. In FIG. 2D, scavenging lumen 96 is a separate lumen running alongside lumen 95. In FIG. 2E, the whole apparatus of FIG. 2B partially fills a circumferential wall 101B, and gas returns along the unoccupied internal volume of circumferential wall 101B.

It is noted that in the illustrated configuration of the embodiment of FIG. 2E, circumferential wall 101B effectively defines the distal diameter of antechamber 20, and removal of scavenged gas can occur without gas ever having to leave antechamber 20. Optionally, circumferential wall 101 is extended distally out of overtube 101B; antechamber 20 is then defined as described for FIG. 2B, and gas is scavenged after it escapes antechamber 20. In effect, this produces a variable-aperture antechamber 20, which is a potential advantage for selecting between targeting treatment over a wider surface area, or a narrow selection.

In some embodiments, circumferential wall 101B comprises an overtube, (e.g., a wall of a working channel or catheter) along which circumferential wall 101 is freely longitudinally advanced. In some embodiments, circumferential wall 101B is positioned in a fixed or limited-adjustment (e.g., adjusted to within up to 5 mm or 10 mm) longitudinal relationship to circumferential wall 101. Optionally, circumferential wall 101 is free to move radially within circumferential wall 101B. Optionally, circumferential wall 101 is held to a fixed or adjustable radial position, e.g., by means of a spacer.

Figure 3B:
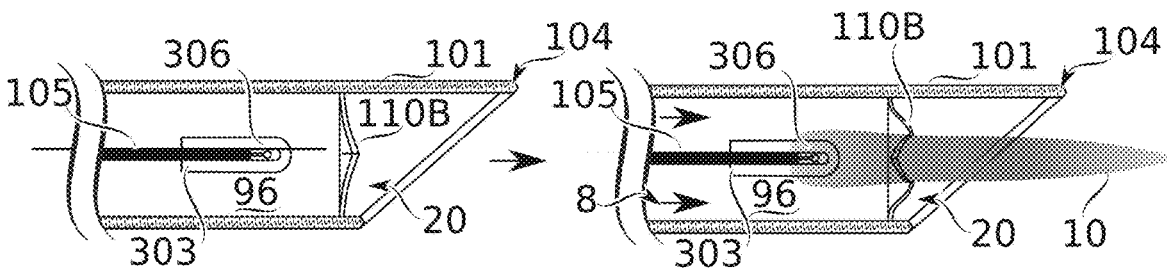
Figure 3C:
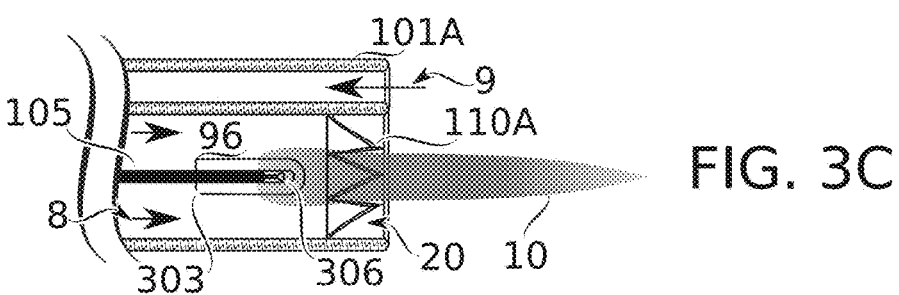
Figure 3D:
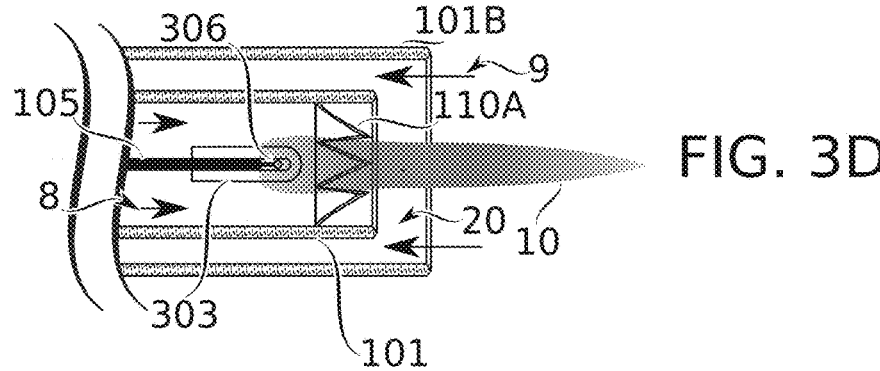

Reference is now made to FIGS. 3A-3F, which schematically represent valved configurations of plasma delivery tips which generate plasma using a flow of ionization gas 8 flowing along a lumen within which a discharge electrode 306 is positioned, according to some embodiments of the present disclosure. FIGS. 3A-3B show both closed (left panel) and open (right panel) configurations of a same respective embodiment.

FIGS. 3A-3D generally correspond to the embodiments of FIGS. 2B-2E, respectively, with the exception that the plasma generating region 12 is now implemented by flowing ionization gas 8 around a discharge electrode 306 positioned within lumen 96 and insulated from the ionization gas 8 by a surrounding dielectric barrier layer 303.

FIG. 3B illustrates a slit valve 110B (also unidirectional), which is optionally provided to any of the embodiments, e.g., of FIGS. 2A-3D in place of leaf valve 110A.

FIG. 3E shows a longitudinally extended valve 110D which is optionally implemented as a piezoelectric one-way valve. Even though it is not primarily pressure-actuated, valve 110D is optionally opened only when there is an increased proximal-side gas pressure (to prevent fluid ingress). For example, valve 110D is opened under the control of a controller 55 that also controls delivery of ionization gas. Electrical conduit 311 delivers voltage to a valve member comprising piezoelectric material layer 331, and conductor layer 330. Differential bending as a result of the imposed electrical field causes valve 110D to open (assuming the valve is normally closed; the actuation to open/close is optionally configured differently, e.g. reversed). Such as valve configuration is optionally used, e.g., with any of the valved embodiments of FIGS. 2B-3D.

FIG. 3F (otherwise similar, e.g., to FIG. 3B) has a one-way flap valve 110E (or another asymmetrically opening valve design). Optionally, the asymmetry of the opening of valve 110E is used to affect the directionality of plasma plume 10. The three panes of FIG. 3F (left, center, right) show three different conditions of valve opening (closed, half open, almost fully open). Optionally, a degree of valve opening is controlled by the pressure of a flow of ionization gas 8. The flap of valve 110E may tend to quench plasma that reaches it. One way to mitigate this is to provide the flap of valve 110E with a charge that tends to deflect the plasma.

Once again, it should be understood that the valve designs described herein are examples, and there is no particular limitation of particular embodiments to work only with valve configurations shown.

Reference is now made to FIGS. 4A-4C, which schematically represent distal-side views of different valve designs, according to some embodiments of the present disclosure. FIG. 4A corresponds to a distal-side view of flap valve 110E (i.e., the valve 110E shown from the side in FIG. 3F). FIG. 4B corresponds to a distal-side view of slit valve 110B (i.e., the valve 110B shown from the side in FIG. 3B). FIG. 4B corresponds to a distal-side view of leaf valve 110A (i.e., the valve 110A shown from the side in, for example, FIG. 3A).

Figures 5A, 5B, 5C, 5D:
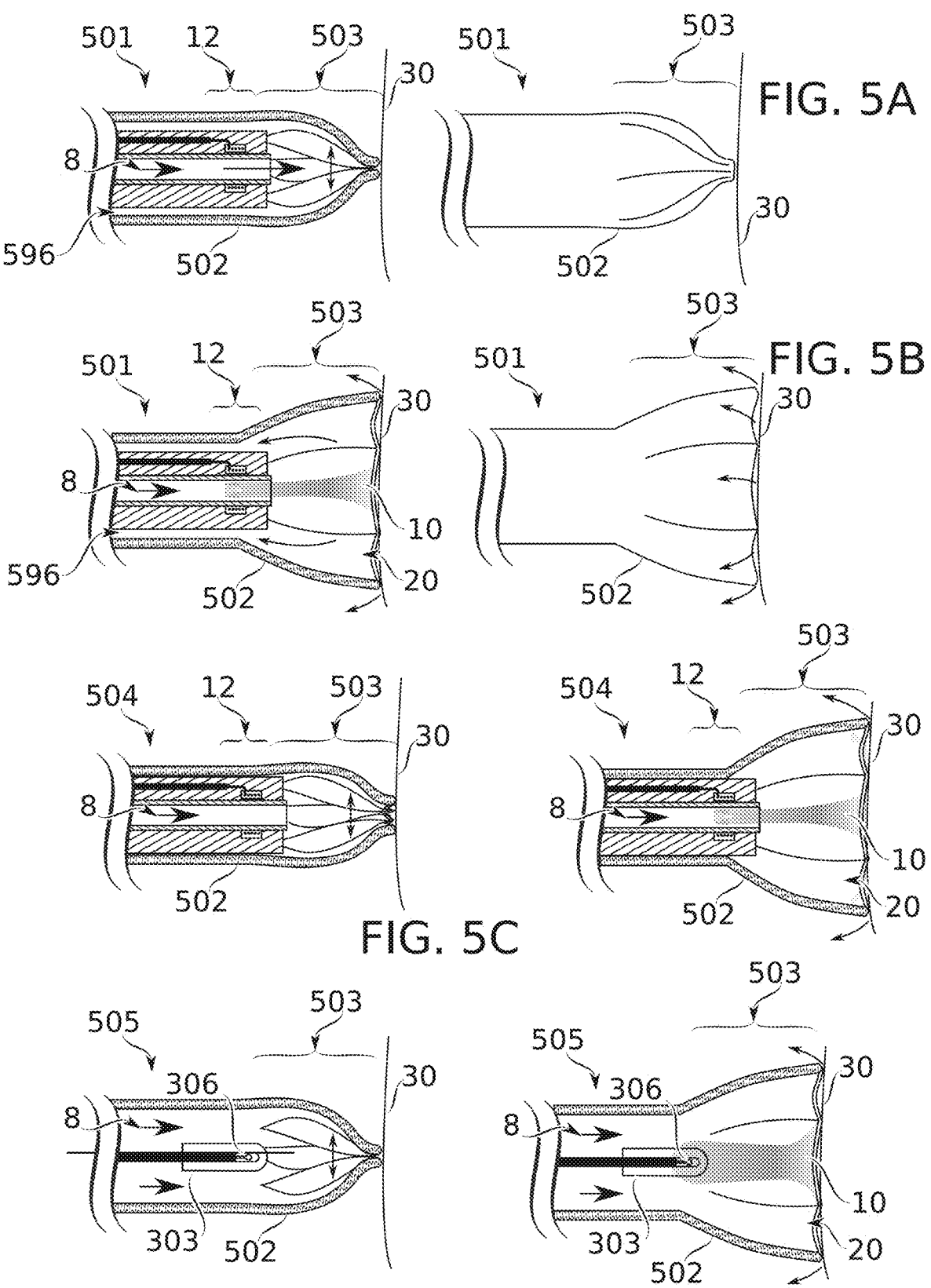
FIGS. 5A-5B schematically represent views of an expandable-tip plasma delivery tip in collapsed (FIG. 5A) and expanded (FIG. 5B) configurations, respectively, according to some embodiments of the present disclosure.
FIG. 5C schematically represents, in cutaway, an expandable-tip plasma delivery tip in collapsed and expanded configurations, according to some embodiments of the present disclosure.
FIG. 5D schematically represents, in cutaway, an expandable-tip plasma delivery tip in collapsed and expanded configurations, according to some embodiments of the present disclosure.

Reference is now made to FIGS. 5A-5B, which schematically represent views of an expandable-tip plasma delivery tip 501 in collapsed (FIG. 5A) and expanded (FIG. 5B) configurations, respectively, according to some embodiments of the present disclosure. The left panels show cutaway views, the right panels shown exterior views. Reference is also made to FIG. 5C, which schematically represents, in cutaway, an expandable-tip plasma delivery tip 504 in collapsed and expanded configurations, according to some embodiments of the present disclosure. The left panel shows a collapsed view; the right panel shows an expanded view. Plasma delivery tips 501, 504 illustrate structural variants of some features of an expanding plasma delivery tip.

In some embodiments, plasma delivery tip 501, 504 comprises a plasma generating region 12 configured to generate plasma from a flow of ionization gas 8 flowing along a lumen around which a circumferentially positioned discharge electrode extends, for example as described in relation to FIGS. 2B-2E, herein. The plasma generating region 12 is sheathed in an expandable sheath 502. When collapsed (FIG. 5A) expandable sheath 502 is substantially sealed against liquid ingress through its distal end 503. Upon expansion, distal end 503 of expandable sheath 502 flares, to create an antechamber 20, which optionally has a distal outer diameter 1.5×, 2×, or greater than an outer diameter of the expandable sheath 502 more proximally. This potentially allows simultaneous delivery of a plasma plume 10 to a correspondingly larger area of target surface 30. Expandable plasma delivery tip 501, 504 also provides a potential advantage to resist clogging (e.g., during device advance), since antechamber 20 remains entirely closed off from the external environment until distal end 503 is expanded and/or pressure from ionization gas 8 is exerted. It is noted that the treatment area is optionally reduced by pressing distal tip 501, 504 even more distally until the antechamber 20 created by distal end 503 is substantially excluded from the flow of plasma (and possibly collapsed or even everted), and the plasma generating region 12 is itself touching or almost touching the target surface 30. This potentially provides a selectably variable treatment area capability to a plasma delivery tip.

In some embodiments, distal end 503 is normally closed; for example, elastically and/or magnetically predisposed to be collapsed. In some embodiments, distal end 503 comprises elastic (e.g., nitinol, glass fiber, or polymer) struts linked by a thin webbing, or an elastic material (e.g., rubber) predisposed by its shape to contract to the collapsed configuration. In some embodiments, conversion from the collapsed to the expanded tip is actuated by pressure from the flow of ionization gas 8. Optionally, or additionally, the conversion is actuated by another method; for example, piezoelectrically-activated bending and/or mechanical actuation (e.g., by pulling, pushing, or rotating a control member).

In some embodiments, flaring actuation of distal end 503 exploits thermally-actuated shape-memory properties. For example, the device may be elastically disposed to close at body temperature, and elastically disposed to open at a lower (preferably) or higher temperature. Optionally, distal end 503 is configured using materials in shapes predisposed to deform elastically toward opposing configurations—toward collapse, or toward expansion. At body temperature or above, the balance of forces between these two is configured to induce collapse. Nitinol shape memory alloys tend to soften (and lose elasticity) below their critical temperature. At least some of the collapsing-disposed struts, in some embodiments, are formed from a nitinol allow which undergoes this softening between body temperature and the temperature of the cold plasma (e.g., between about 37° C. and about 25° C.). Upon softening, the balance of forces changes, allowing distal end 503 to expand. This is optionally implemented using struts of two different nitinol alloys (that is, with different transition temperatures), struts of a nitinol alloy acting against a rubber polymer predisposed to assume an expanded shape, or another construction.

Target surface 30 provides closure to the aperture of antechamber 20 when distal end 503 is pressed against it, helping to maintain sufficient internal pressure for inflation. At least at or above this pressure, ionization gas 8 escapes around the distal edges of flaring distal end 503, and/or is scavenged (e.g., as shown for plasma delivery tip 501) through one or more gas scavenging lumens 596 (FIGS. 5A-5B). Potentially, scavenging gas actively helps to maintain consistency of the "inflation" state of expanded distal end 503.

In some embodiments, distal end 503 is self-expanding if not held closed by, e.g, adhesive and/or confinement by another structure. Scavenging via gas scavenging lumen(s) 596 may be operated under active suction. This potentially prevents leakage of gas around the distal edges of flaring distal end 503. Optionally, the suction helps to clear fluid from the volume enclosed by flaring distal end 503. In some embodiments, the cleared volume is established within a surrounding liquid-filled environment (such as a heart chamber, for example), e.g., using suction onto target surface 30 to create an isolated chamber, from which fluid is evacuated by suction, allowing plasma treatment to be applied.

Brief reference is made to FIG. 5D, which schematically represents, in cutaway, an expandable-tip plasma delivery tip 505 in collapsed and expanded configurations, according to some embodiments of the present disclosure. Plasma delivery tip 505 uses a configuration of a dielectric barrier layer 303 and plasma discharge electrode 306 which are positioned within a flow of ionization gas 8. This type of plasma generating tip apparatus is optionally configured for use with the same features of an expandable sheath 502 and distal end 503 described in relation to FIGS. 5A-5C (or FIG. 5E).

Sealing of the tip of flaring distal end 503 in its closed configuration is optionally achieved by holding it closed enough (e.g., as it is predisposed elastically) that any residual small aperture at its tip is resistant to wetting, e.g., due to surface tension of liquids it may be immersed in. The tip material is optionally normally hydrophobic, or treated with a hydrophobic coating. The tip may be configured with webbing material thinned and/or folded in and out of the way to get a more pointed tip, (e.g., as shown in FIG. 5A), or blunter tip (FIG. 5C). Optionally, a secondary seal is provided within flaring distal end 503, for example as short leaves which meet when distal end 503 is collapsed, and are pulled out of the way when distal end 503 expands. Optionally, a secondary seal is provided outside of flaring distal end; for example, in the form a "calyx", e.g., as described in relation to FIG. 5E.

Optionally, distal end 503 is initially closed by bonds (e.g., adhesive bonds and/or thin bridges of interconnecting material) which break upon expansion. It should be noted that reliance on a one-time closure mechanism potentially interferes with re-deployment after device withdrawal, but this may be acceptable in some applications (e.g., single-use, single-target applications). Optionally, distal end 503 is configured (e.g., by use of an internal surface coating) to self-adhere. After expansion, distal end 503 can be reset to a collapsed configuration by withdrawal into a confining lumen, sticking the surfaces of distal end 503 to stick to each other and restoring a closed and self-sealed configuration.

Figures 5E, 5F:
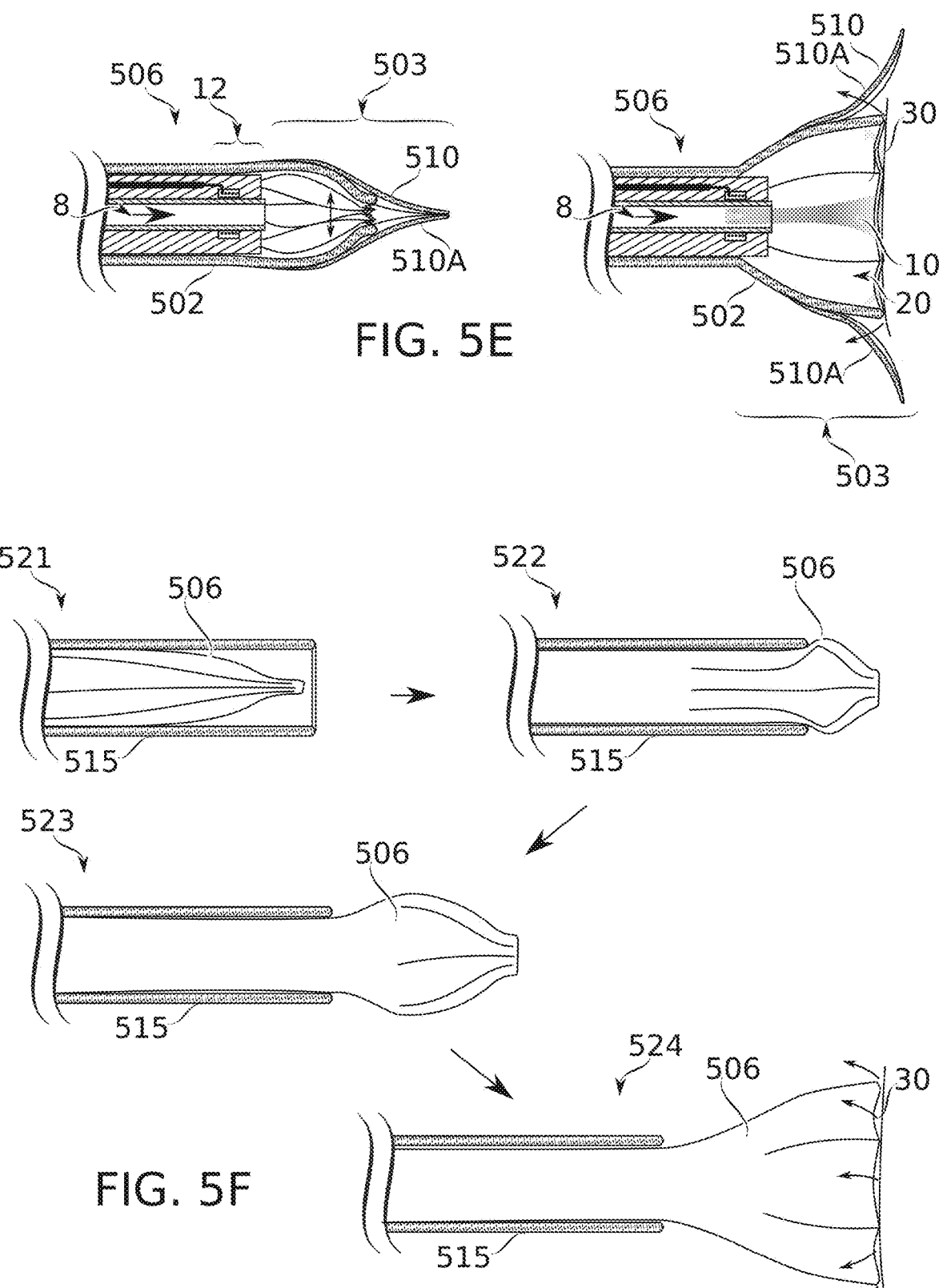
FIG. 5E schematically represents in cutaway, an expandable-tip plasma delivery tip in collapsed and expanded configurations, and comprising a calyx, according to some embodiments of the present disclosure.
FIG. 5F schematically illustrates deployment of a self-expanding distal end from an introducer, according to some embodiments of the present disclosure.

Reference is now made to FIG. 5E, which schematically represents in cutaway, an expandable-tip plasma delivery tip 506 in collapsed and expanded configurations, and comprising a calyx 510, according to some embodiments of the present disclosure.

Expandable plasma delivery tip 506 is generally configured like one of the expandable plasma delivery tips of FIGS. 5A-5D, with the addition of a calyx 510. A calyx 510 is optionally provided, for example, to enhance sealing and/or provide a thinner and/or sharper point to a distal end 503 when it is in its collapsed configuration. It is noted that a more tapered configuration provides a potential advantage for using a plasma delivery tip 66 in navigating narrow body lumens; and/or in penetrating, for example, solid tissue, body lumen walls and/or tissue membranes. The use of sharper angles and/or smaller apertures may also help to exclude fluid due to surface tension effects.

Calyx 510 comprises one or more leaves 510A (or, by botanical analogy, "sepals" 510A) which attach on a proximal side to an exterior of the plasma delivery tip 506. They are shaped to close off a distal end of the plasma deliver tip when they are collapsed, and split apart (without being joined by fully circumferential webbing) when distal end 503 expands. Optionally, calyx 510 tapers to a thin tip distally. Optionally, the leaves 510A are configured to attach to and/or overlap each other (and/or themselves) when collapsed. Optionally, the leaves 510A themselves are interconnected by a membrane along at least a portion of their length, potentially enhancing their ability to provide a contaminant-excluding seal.

Calyx 510 is optionally predisposed to be collapsed, e.g., elastically and/or magnetically. Optionally calyx 510 is held shut by bonding (e.g., adhesive) and/or a sacrificial membrane which breaks when distal end 503 is expanded. Optionally calyx 510 is self-adherent to assist in restoring a collapsed configuration, e.g., upon withdrawal of distal tip 503 into a confining lumen.

Optionally, calyx 510 is formed primarily of a soft and flexible material, e.g., to provide an atraumatic tip. In some embodiments, calyx 510 is more thorn- or needle-like; e.g., comprising a metallic and/or hard plastic portion (optionally sharpened). This potentially assists in tissue penetration and/or manipulation; e.g., penetration to reach a plasma treatment target, and/or to prepare (e.g., dissect in situ and/or make more permeable) a plasma treatment target.

It is noted that calyx 510 may be considered a type of "external valve" which can be opened, e.g., by pressure from within; but still protects (while it is closed) against contaminant ingress. Optionally, calyx 510 is provided to seal of a distal end of a non-expanding antechamber 20, for example, a distal end of one of the embodiments of FIGS. 2A-3F (in the case of FIGS. 2B-3F, the interior valve is optionally retained or omitted). When closed, the calyx 510 acts to prevent contaminant ingress, but when open, it does not define the antechamber 20; rather, it peels away into disconnected sections, revealing antechamber 20 positioned underneath and/or proximally.

Reference is now made to FIG. 5F, which schematically illustrates deployment of a self-expanding distal end 506 from an introducer 515, according to some embodiments of the present disclosure. Distal end 506 (used in plasma delivery, for example, as described in relation to distal end 503) elastically is predisposed to expand, but held closed by introducer 515, e.g., held collapsed within a lumen of introducer 515. Panel 521 shows distal end 506 entirely sheathed by introducer 515. Panels 522, 523 show expansion during unseating of distal end 506, and panel 524 shows distal end 506 fully unsheathed, in contact with target surface 30, and with a flow of ionization gas (arrows pointing away from surface 30) escaping it under pressure. Plasma Treatment Methods and Scenarios Reference is now made to FIGS. 6A-6C, which schematically represent access modes allowing providing plasma to a plasma treatment target 1603 positioned within lungs 20, according to some embodiments of the present disclosure. Further reference is made to FIG. 6D, which provides a detail view of an example of a plasma delivery configuration corresponding to FIG. 6C, according to some embodiments of the present disclosure. Reference is also made to FIG. 6E, which is a schematic flowchart of a method of plasma treatment within a body lumen, according to some embodiments of the present disclosure.

Figures 6A, 6B:
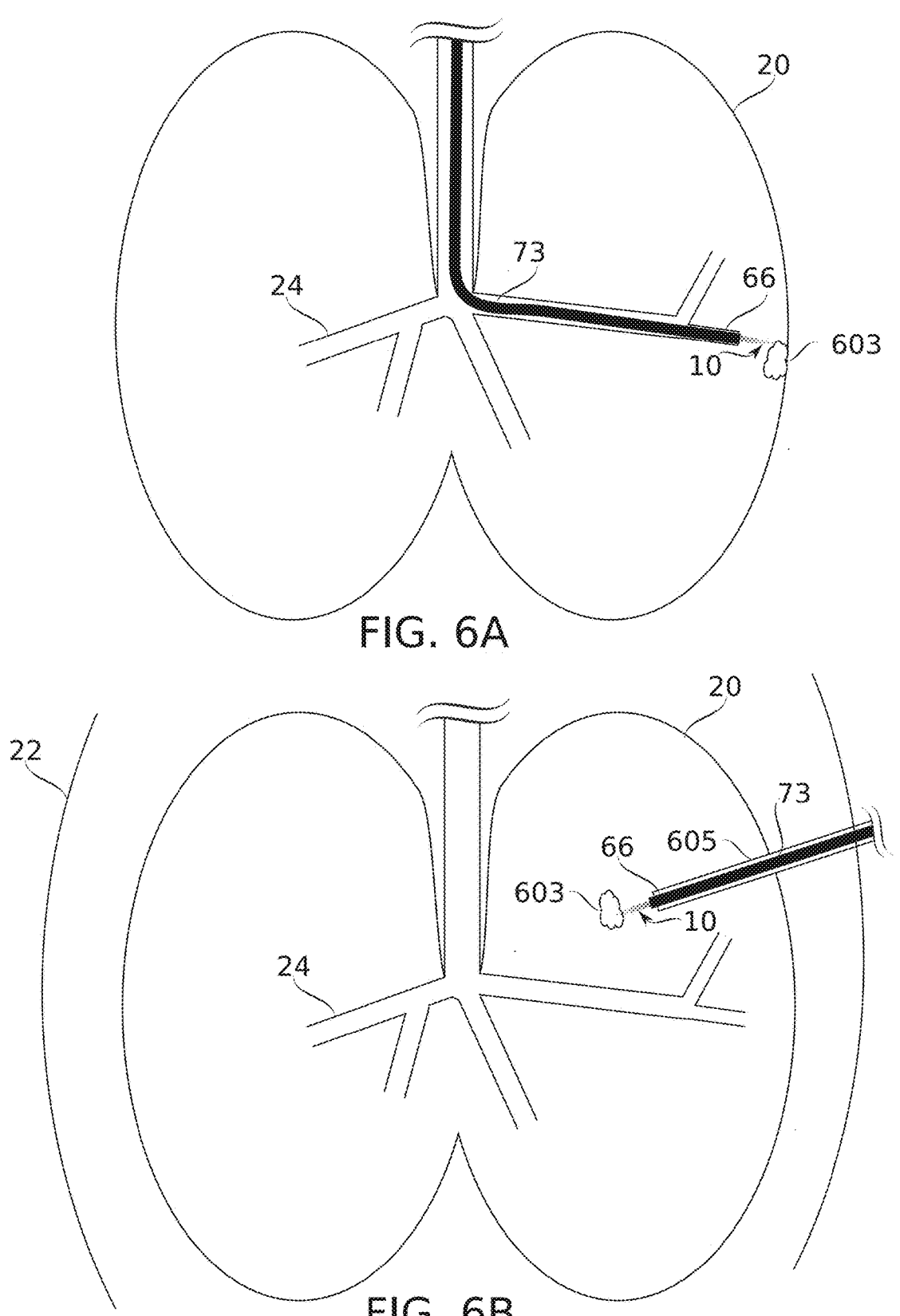
FIGS. 6A-6C schematically represent access modes allowing providing plasma to a plasma treatment target positioned within lungs, according to some embodiments of the present disclosure.

In FIG. 6A, probe conduit 73 has been introduced through the trachea and bronchi 24 of lung 20, and advanced (e.g., under image guidance) until it is positioned within range of target 603, wherefrom it generates plasma plume 10.

In FIG. 6B, probe conduit 73 has been introduced percutaneously (across body wall 22) through an introducer 605, to a position within range of target 603, wherefrom it generates plasma plume 10.

Figure 6C:
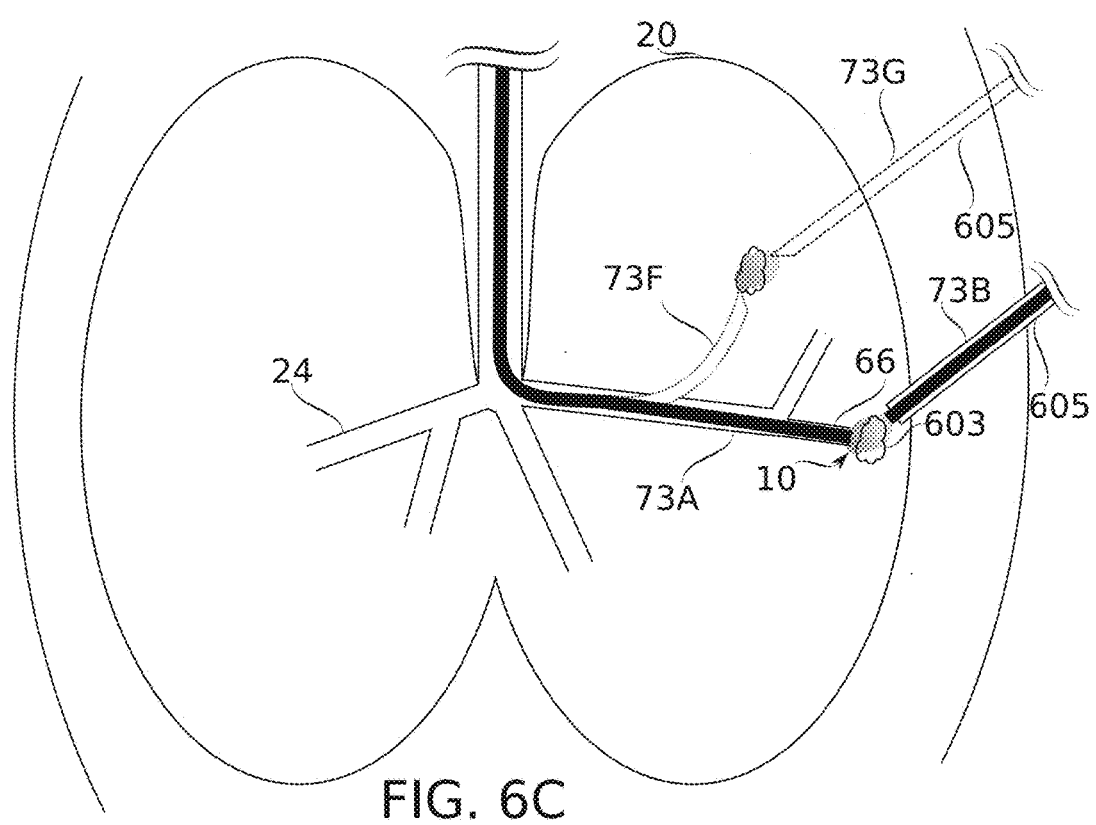

In FIG. 6C, first probe 73A has been introduced through the trachea and bronchi 24 of lung 20, and advanced (e.g., under image guidance) until it is positioned within range of target 603. Second probe 73B has been introduced percutaneously (across body wall 22) through an introducer 605, to a position within range of target 603. Operated together, probes 73A, 73B generate plasma plume 10. Either of the probes 73A, 73B may be the voltage supply, either may be the supplier of ionization gas and/or fluid comprising supplementary species, and optionally either may provide an evacuation lumen used to exhaust provided fluid. Probes 73F, 73G show alternative probe placements, with probe 73G in this case comprising a trocar, and probe 73F a sharpened tip which has been steered from a tracheal/bronchial pathway to penetrate into the parenchyma of the lung. Optionally blood vessels (veins in particular) are used for such a hybrid pathway, with the probe being brought to the general vicinity of a target tissue via blood vessels of sufficient diameter, then deviated through the vascular wall to reach the target itself. Positioning of any one or more of the probes may be accomplished under manual control and/or by use of a robotic positioning system.

Figure 6D:
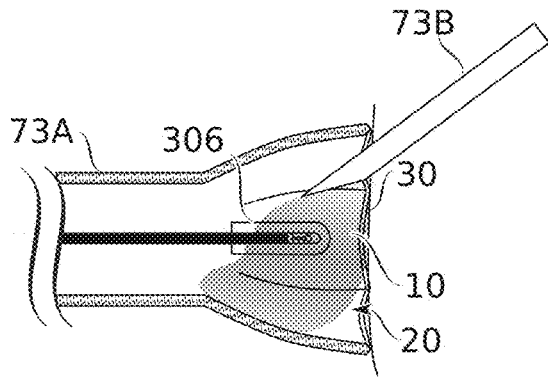
FIG. 6D provides a detail view of an example of a plasma delivery configuration corresponding to FIG. 6C, according to some embodiments of the present disclosure.
Figure 6E:
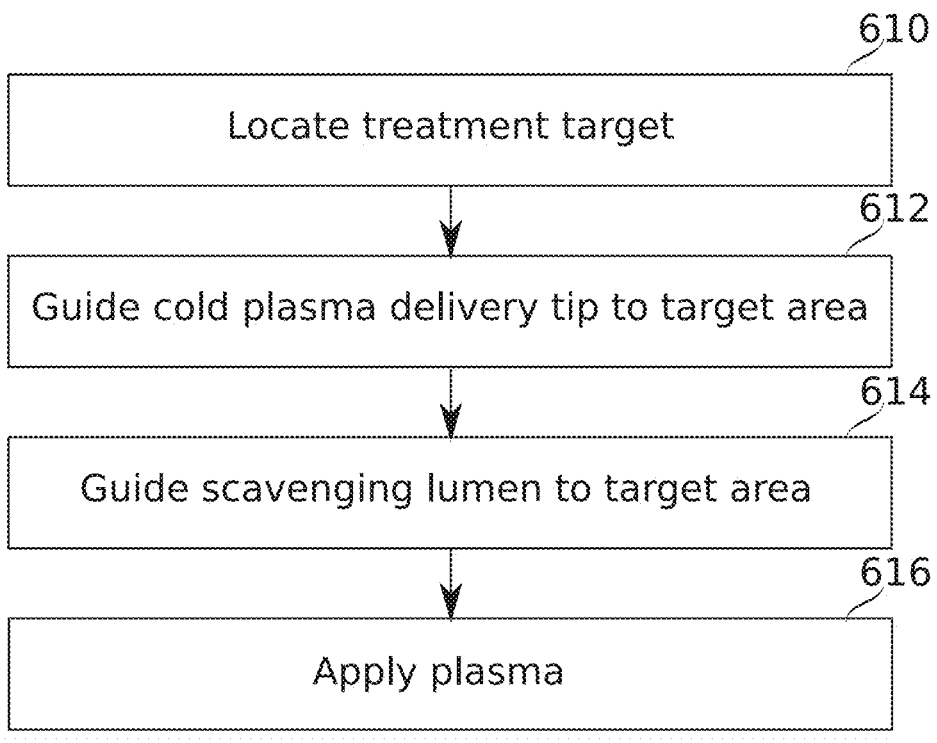
FIG. 6E is a schematic flowchart of a method of plasma treatment within a body lumen, according to some embodiments of the present disclosure.

FIG. 6D shows in closer detail how an example of how the scenario of FIG. 6C may be configured. In the example shown, probe 73A is a hooded plasma delivery tip (optionally one as described in relation to FIG. 5D) introduced through the trachea and bronchi, and brought into apposition with a target surface 30 which is to be treated by exposure to plasma. In this example, probe 73A provides the voltage via discharge electrode assembly 306. Alternatively a lumen-circumferential electrode is provided as a discharge electrode. Trocar 73B has been percutaneously introduced through surface 30 into the hood of probe 73A, wherefrom it may perform either or both of the functions of delivering fluid (e.g., ionization gas), and exhausting it. Plasma 10 is generated where ionization gas flows over discharge electrode assembly 306, redistributing according to the flow of gas, which may come to fill the entire hood region. A lumen of probe 73A may be used to exhaust gas that probe 73B supplies, or to supply gas that probe 73B exhausts. Suction may be used to create a slight negative pressure, with the potential advantages of preventing the leakage of gas into the environment surrounding the probes 73A, 73B, and optionally also of clearing the plasma working volume of potential contaminants.

Alternatively, gas may be vented around the edges of the hood as described in relation to FIG. 5D. Optionally, lumens of both probes 73A and 73 are used to provide fluid inputs to the treatment region; for example, one of the probes supplies ionization gas, and that other supplies fluid comprising supplementary species such as nitrogen, oxygen, and/or water molecules.

Referring to the method of FIG. 6E in the context of FIGS. 6A-6B: corresponding to block 610, in some embodiments, the target is located, for example, using MRI imaging, CAT imaging, PET imaging, or another method.

Corresponding to block 612, in some embodiments, the plasma delivery tip 66 is guided to the region of target 603 through an introducer 605 via a percutaneous incision (FIG. 6B), or via a catheter system or acting as its own navigation device (FIG. 6A). Plasma delivery tips 66 are optionally provided with sharpened ends (e.g., trocar or sharpened-point shaped), or atraumatic ends. Probe conduits 73 equipped with a plasma delivery tip 66 are optionally steerable, optionally provided with a working channel which accepts a guidewire (or other tooling), and/or optionally themselves inserted through the working channel of a catheter device or endoscope.

Trocar-tipped embodiments are described, for example, in relation to FIG. 2C, 3B, or 3F; sharp-tipped or atraumatic expandable embodiments, are described, for example, in relation to FIGS. 5A-5E. Optionally, a blunt-ended plasma delivery tip 66 is used. Arrangements for preparing a target region 603 are optionally selected from among those described in relation to target region 703.

Corresponding to block 614, in some embodiments, the use of an auxiliary scavenging lumen is optional. In some embodiments, no scavenging is needed (e.g., gas escapes through the bronchi and trachea). Optionally, probe conduit 73 itself is provided with one or more gas scavenging lumens. If used, an auxiliary scavenging lumen can be introduced by any suitable means. Optionally, the distal end of a standard catheter system is introduced to the vicinity of the target 603, and used to evacuate ionization gas passive (as pressure at the treatment sit forces gas through it), and/or under negative pressure.

Corresponding to block 616, in some embodiments, the area of target 603 is treated with plasma. Liquid exclusion may or may not be a problem, depending on the state of the lungs and the position of target 603. Several examples of how a plasma delivery tip 66 may be moved during treatment are described in relation to FIG. 7A-C, which also apply as options available with the examples of FIGS. 6A-6B.

Figure 7A:
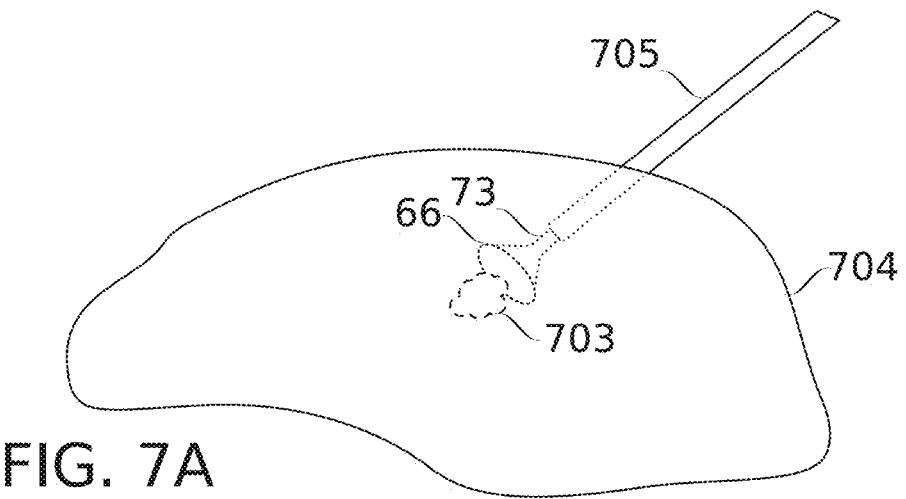
FIGS. 7A-7C schematically represent application of plasma treatment to a target in a solid organ, according to some embodiments of the present disclosure.
Figure 7B:
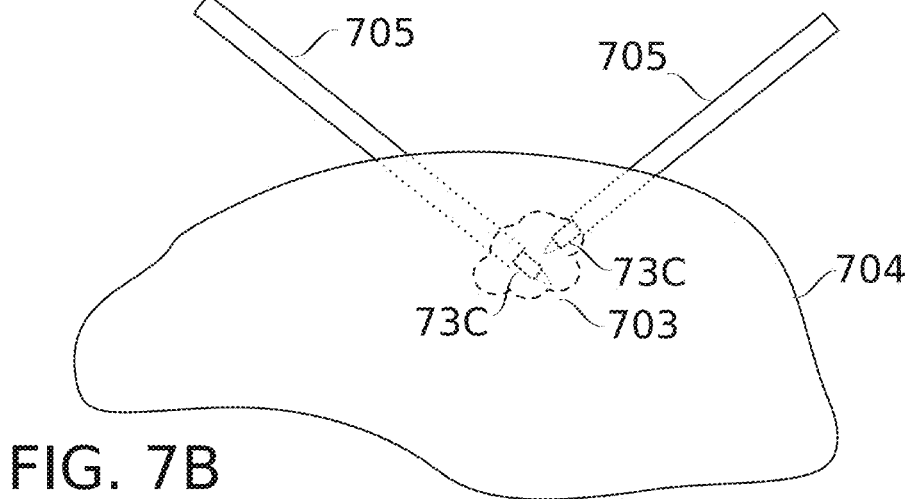
Figure 7C:
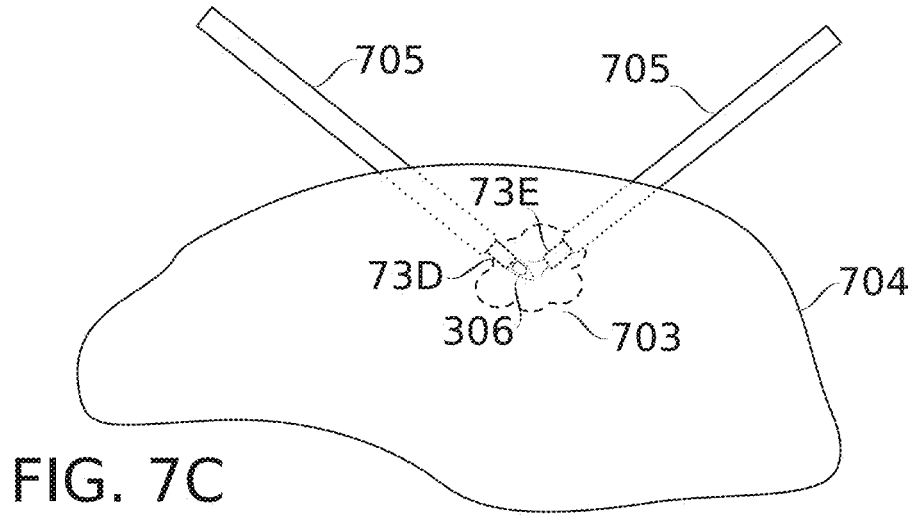

Reference is now made to FIGS. 7A-7C, which schematically represent application of plasma treatment to a target 703 in a solid organ 704, according to some embodiments of the present disclosure. In FIG. 7A, probe 73 is shown inserted to the region of a target 703 within a solid organ 74 (for example, a liver). In the example of FIG. 7A, plasma delivery tip 66 comprises an expandable distal end. In FIG. 7B, one or more probes 73C are introduced from different angles (simultaneously or at different times) to allow treatment of different region of target 703. In FIG. 7C, plasma is generated using a probe 73D comprising a discharge electrode assembly 306, positioned with ionization gas delivered by a second probe 73E. Using a plurality of probes, the functions of ionization gas delivery, electrical power delivery (ionization), and ionization gas ventilation are optionally performed by any given probe in any given combination; for example: gas delivery and gas ventilation, gas delivery and ionization, and/or gas ventilation and ionization (with at least the remaining function handled by another of the plurality of probes). These three functions are optionally divided among three probes, each of which handles one of the functions. Functions can also be duplicated; for example, a plurality of probes performing any of the functions of gas delivery and gas ventilation, gas delivery and ionization, and/or gas ventilation and ionization. Optionally, supplementary species are provided by a probe in combination with or separately from any of the other three functions just named.

Optionally, a target on an exterior surface of the solid organ and/or on a surface between lobes of the solid organ is targeted. The target comprises, for example, a tumorous region, or region of pathogenic infection (e.g., bacterial, viral, and/or fungal).

Referring to the method of FIG. 6E in the context of FIGS. 7A-7C: corresponding to block 610, the target is located, for example, using MRI imaging, CAT imaging, PET imaging, or another method.

Corresponding to block 612, the plasma delivery tip 66 and/or other probe 73C-73E is guided to the target region through an introducer 705 via a percutaneous incision. If necessary, the organ itself is penetrated using standard devices such as a needle and/or trocar. Optionally, a sharp-tipped embodiment of a plasma delivery tip 66 is used; for example, a trocar-tipped embodiment such as is described in relation to FIG. 2C, 3B, or 3F; or a sharp-tipped expandable embodiment, for example a version of the embodiment of FIG. 5E with a sharp and stiff calyx 510. Optionally, the target 703 is prepared for plasma treatment by incision or other partial dissection, which potentially increases the surface area directly exposed to plasma; and/or loosens the treatment area to allow greater expansion of the plasma deliver tip.

Corresponding to block 614: for operation within an abdominal cavity (which is anyway typically insufflated) a separate gas scavenging lumen is optionally omitted. However, for deeply embedded targets 703, there may be a tendency for ionization gas to inflate and/or destabilize the working area. For this or another reason, a gas scavenging lumen may be inserted where it will retrieve ionization gas used for generating plasma.

Corresponding to block 616: plasma is actually generated and delivered. This delivery may accompany and/or be performed after expansion of a plasma delivery tip 66 (the expansion being to the degree which spatial constraints allow). Optionally, plasma delivery is performed with tip 66 pressed flush up against a portion of the target 703, making use of an antechamber 20 to create a liquid-free region. Optionally, tip 66 is inserted into a "pocket" from which liquid flushed out (e.g., by the ionization gas), allowing deliver of plasma from positions a few millimeters more remote from the tissue surface. Plasma is optionally delivered in a sequence of several activations along a track extending through the target 703 as the plasma delivery tip 66 is gradually inserted to the target (i.e., inserted, inflated, operated, collapsed, inserted slightly more deeply, and repeating). Additionally or alternatively, plasma delivery is performed during withdrawal of the plasma delivery tip. Sufficiently large targets 703 optionally receive plasma treatment in a plurality of passes, e.g., along a plurality of insertion tracks passing through the target region. Optionally or alternatively, treatment is applied superficially to a target region surface and/or a surface overlying a shallowly-placed target region, allowing scanning of the plasma delivery tip 66 over the surface.

Figures 8A, 8B:
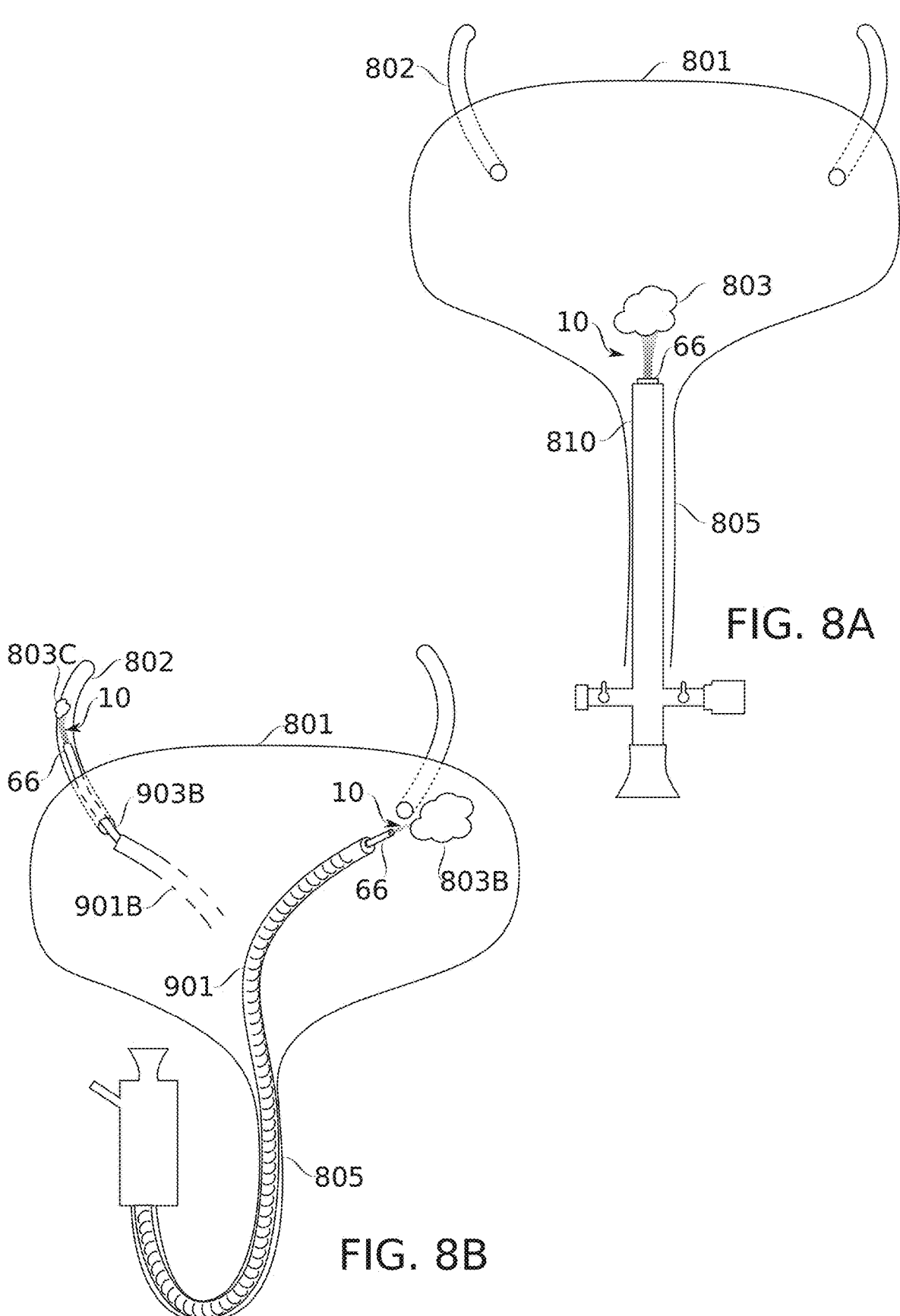
FIGS. 8A-8B schematically represent application of plasma treatment to targets in a urinary tract, according to some embodiments of the present disclosure.

Reference is now made to FIGS. 8A-8B, which schematically represent application of plasma treatment to targets in a urinary tract, according to some embodiments of the present disclosure. FIG. 8A illustrates treatment using a rigid cystoscope 810 inserted along a urethra 805, while FIG. 8B illustrates treatment using a flexible cystoscope 901 inserted along urethra 805.

Referring now to the method of FIG. 6E in the context of FIGS. 8A-8B: corresponding to block 610, the target is located, for example, endoscopically using the cystoscope.

Corresponding to block 612, in some embodiments, the plasma delivery tip 66 is guided to the target region through a cystoscope 810, 901 via a urethra. Plasma delivery tip 66 is optionally blunt-ended or provided with a tapered atraumatic end. In some embodiments, a treatment target 803, 803B is located on an inner wall of a bladder 801, where it is directly exposed to plasma plume 10 generated from a plasma delivery tip 66. Optionally (in position 901B) a flexible cystoscope 901 is steered to the bladder inlet of a ureter 802; and from there, plasma deliver tip 66 is navigated to a target 803C positioned deeper within the urinary tract.

Corresponding to block 614, in some embodiments, the use of an auxiliary scavenging lumen is optional. If used, an auxiliary scavenging lumen can be introduced by any suitable means. Optionally, gas scavenging is performed through a separate channel of the cystoscope 805, 901 which is also used to introduce plasma delivery tip 66. Optionally, a dedicated gas scavenging device is introduced, e.g., through another working channel of cystoscope 805, 901. Optionally, plasma delivery tip 66 itself is provided with one or more gas scavenging lumens.

Corresponding to block 616, in some embodiments, the target 803, 803B, 803C is treated with plasma. Liquid exclusion capability within plasma delivery tip 66 is preferable, even if bladder 801 itself is substantially empty, in order to prevent contamination from residual liquid. Liquid may also be encountered in ureter 802, and should be excluded. Several examples of how a plasma delivery tip 66 may be moved during treatment are described in relation to FIG. 7A-C, which also apply as options available with the examples of FIGS. 8A-8B.

Figure 9:
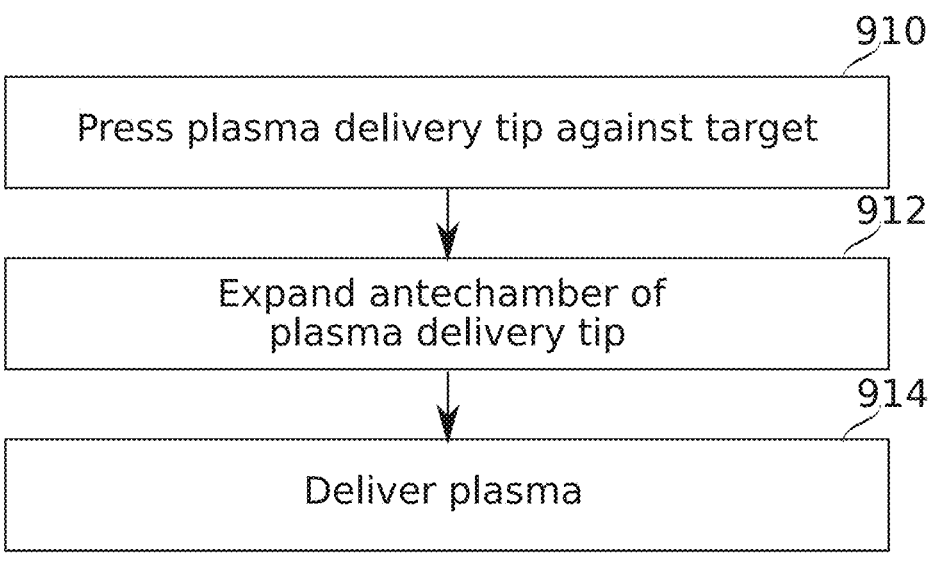
FIG. 9 is a schematic flowchart of a method of delivering plasma to a target within a body lumen, according to some embodiments of the present disclosure.

Reference is now made to FIG. 9, which is a schematic flowchart of a method of delivering plasma to a target within a body lumen, according to some embodiments of the present disclosure.

At block 910, in some embodiments, a distal side of the plasma delivery tip is pressed against a target selected for plasma treatment.

At block 912, in some embodiments, a distal portion of the plasma delivery tip is expanded; optionally by exertion of pressure from ionization gas supplied to the plasma delivery tip which inflates the plasma delivery tip.

At block 914, in some embodiments, the plasma is delivered.

Figure 10:
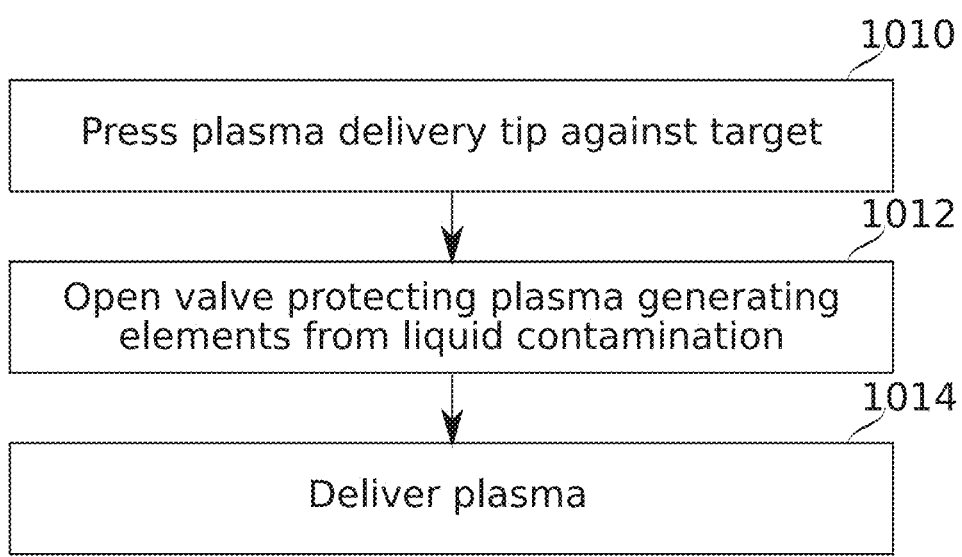
FIG. 10 is a schematic flowchart of a method of delivering plasma to a target within a body lumen, according to some embodiments of the present disclosure.

Reference is now made to FIG. 10, which is a schematic flowchart of a method of delivering plasma to a target within a body lumen, according to some embodiments of the present disclosure.

At block 1010, in some embodiments, a distal side of the plasma delivery tip is pressed against a target selected for plasma treatment.

At block 1012, in some embodiments, a valve of the plasma delivery tip is opened. The valve is configured to protect at least plasma generating elements of the plasma delivery tip (e.g., lumenal surfaces alongside a discharge electrode of the plasma delivery tip) from contamination.

At block 1014, in some embodiments, the plasma is delivered.

Figure 11:
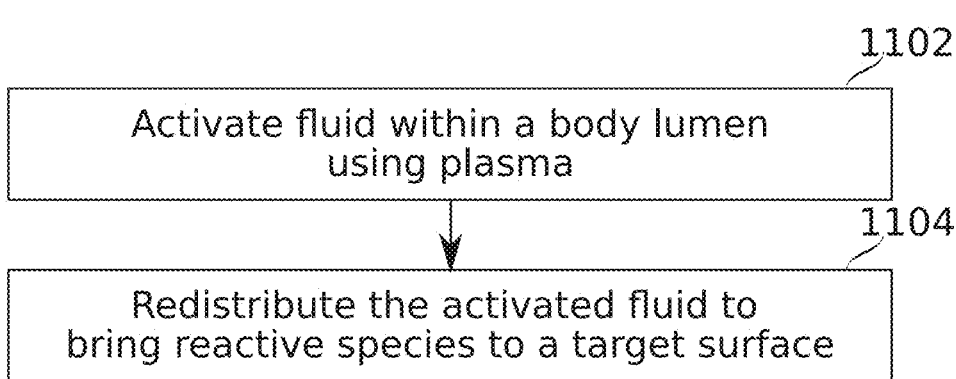
FIG. 11 is a schematic flowchart of a method for delivering plasma-activated fluid to a target surface within a body lumen, according to some embodiments of the present disclosure.

Reference is now made to FIG. 11, which is a schematic flowchart of a method for delivering plasma-activated fluid to a target surface within a body lumen, according to some embodiments of the present disclosure.

At block 1102, in some embodiments, a plasma plume is directed onto environmental fluid within the body lumen. Optionally, the environmental fluid comprises aqueous liquid. Optionally, the environmental fluid comprises a film of aqueous liquid (e.g., of about 1 mm thickness or less) positioned between the target surface and a layer of gaseous fluid. In some embodiments, movement of liquid of the film relative to the surface is dominated by surface-to-surface interactions such as surface tension, cohesion, Van der Waals force, and/or Plateau-Rayleigh instability. Optionally, the aqueous liquid film comprises an aqueous layer overlying a surface of bladder or stomach, and/or another organ of the GI tract or urinary tract. The surface may be an interior lumenal surface of an organ, an outer surface of the organ (e.g., an abdominal organ surface accessed laparoscopically), and/or a tissue surface created by dissection, incision, injection, or another surgical manipulation.

Optionally, the environmental fluid comprises a larger thickness of aqueous fluid overlaying the target surface; e.g., a thickness greater than 1 mm and/or a thickness sufficiently great that the fluid flows primarily under forces of pressure (e.g., gravity) which are independent of surface interactions.

Optionally, the environmental fluid comprises pre-existing and/or naturally present body liquid and/or gas. Optionally, the environmental fluid comprises liquid and/or gas which is artificially introduced to the region of the target surface, e.g., via an introduced delivery lumen. Optionally, the introduced delivery lumen is part of a plasma generating device which generates the plasma plume.

At block 1104, in some embodiments, the activated fluid is redistributed across the target surface. In some embodiments, the redistribution is encouraged by one or more of the following operations, performed during block 1104 and/or previously:

Additional fluid is supplied near the site of fluid activation, forcing the activated fluid outward from the site of fluid activation. Fluid is optionally supplied using a lumen of a plasma delivery device (optionally the gas delivery lumen used to delivery ionization gas), an auxiliary lumen of the plasma delivery device, and/or a lumen of another device. The activated fluid and the fluid used for redistribution are optionally the same or different in composition. In some embodiments, additional fluid is supplied over the course of several minutes (e.g., 10 minutes) up to several hours, or days (e.g., a week or more).

Regions surrounding the site of fluid activation have previously been dried, allowing them to more readily accept (e.g., "sponge up") activated fluid spreading from the site of fluid activation. Optionally, the drying is performed by using gas from a gas delivery lumen which also delivers gas used to generate the plasma, an auxiliary lumen of the plasma delivery device, and/or a lumen of another device.

The activated fluid is agitated, e.g., by directing a jet of gas and/or liquid into the region of the activated fluid. Optionally, the jet is provided from the gas delivery lumen which also delivers gas used to generate the plasma (and may comprise the plasma plume itself). Optionally, agitation is performed using an auxiliary lumen of the plasma delivery device, and/or a lumen of another device.

Figure 12:
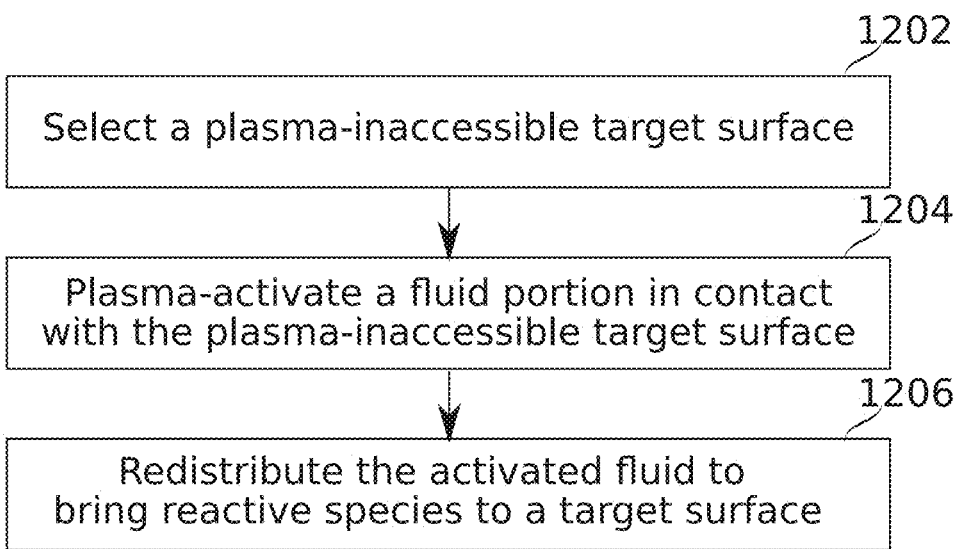
FIG. 12 is a schematic flowchart of a method for delivering plasma-activated fluid to an inaccessible target surface within a body lumen, according to some embodiments of the present disclosure.

Reference is now made to FIG. 12, which is a schematic flowchart of a method for delivering plasma-activated fluid to an inaccessible target surface within a body lumen, according to some embodiments of the present disclosure.

At block 1202, in some embodiments, a target surface is selected which is inaccessible to direct impingement by a plasma plume from a plasma treatment device.

At block 1204, in some embodiments, plasma is directed from the plasma treatment device onto a portion of fluid (optionally, aqueous fluid) which is in contact with the target surface. In some embodiments, the fluid comprises saline. In some embodiments, the fluid comprises a noble gas.

At block 1206, in some embodiments, the activated fluid redistributes to reach the target surface. Optionally, the activated fluid is actively redistributed, for example, using one of the operations described in relation to block 1104 of FIG. 11.

In some lung disease treatments (e.g., severe cases of pneumonia), a patient's lung is flushed with saline, e.g., to help clear mucous. Optionally, plasma generation is performed using a plasma delivery tip operating within the lungs and generating plasma directly onto the saline. Optionally, an outlet aperture of the plasma delivery tip is deliberately immersed into the saline and operated within the saline.

In some lung disease treatments, a patient's lung is treated for an alveoli-obstructing condition (e.g., severe pneumonia), by inflating it with oxygenated helium gas (e.g., avoiding the introduction of pressurized nitrogen). In some embodiments, plasma is generated within the oxygenated helium gas mixture. The helium gas mixture thus serves as the environmental fluid which becomes the activated fluid, allowing distribution of reactive species induced into the activated fluid by the plasma.

In some embodiments, the activated fluid within the body comprises a quantity of, e.g., at least 100 ml, 500 ml, or 1000 ml. The quantity of fluid is optionally flushed and/or renewed; e.g., by maintaining a liquid infusion, and/or periodically. Activation of the fluid is optionally performed continuously, e.g., over a period of several minutes (e.g., 10 minutes), hours (e.g., 10 hours), or days. By the continuous activation, a long-standing exposure of a treatment target to plasma-induced reactive species may be obtained. Optionally, the plasma delivery device, once positioned, is be operated without active navigation or other direct supervision being constantly required. Optionally, a plasma delivery tip of the plasma delivery device is placed in a convenient intrabody location in fluid communication with the treatment target, but not inserted so deeply within to the body cavity as to prevent remaining in place for an extended period of time without constant direct supervision.

The distance between the plasma delivery tip and a target surface to be treated is optionally several centimeters separated by the activated fluid, e.g., at least 3 cm, 4 cm, 5 cm, 10 cm, or another distance.

In some embodiments, for example, a bladder or other hollow organ is treated by maintaining it filled with several milliliters of liquid (e.g., at least 50 ml of fluid), within which reactive species are continuously induced by the operation of a plasma delivery tip of a plasma treatment device.

Plasma Treatment in Fluid-Filled Lumens

Figure 13A:
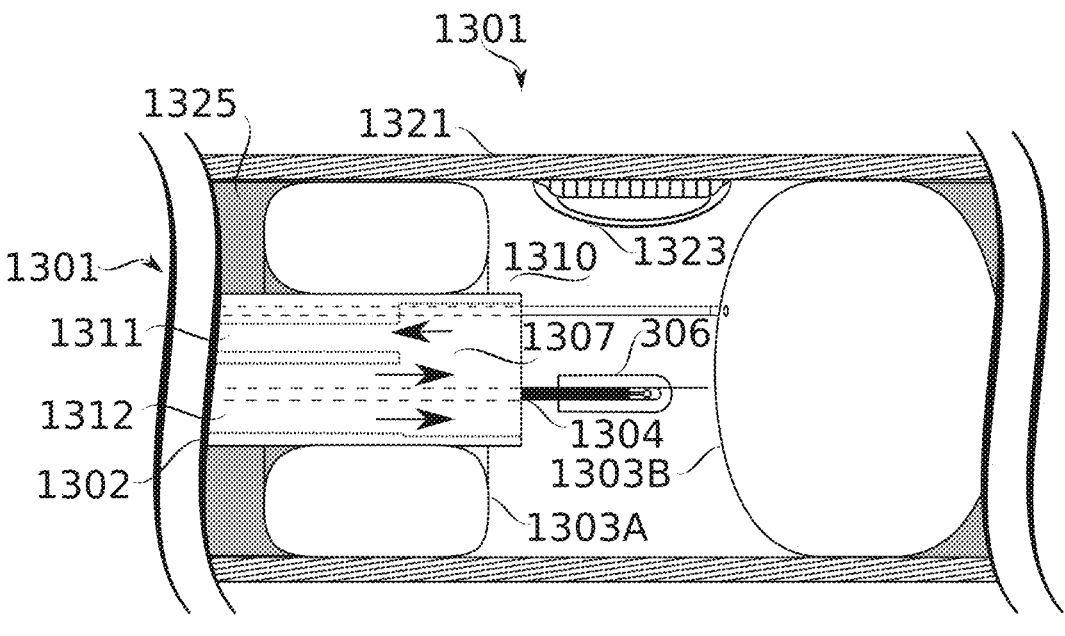
FIGS. 13A-13B schematically represent plasma delivery devices, operated to deliver plasma within lumenal spaces, established by the inflation of balloons, according to some embodiments of the present disclosure.
Figure 13B:
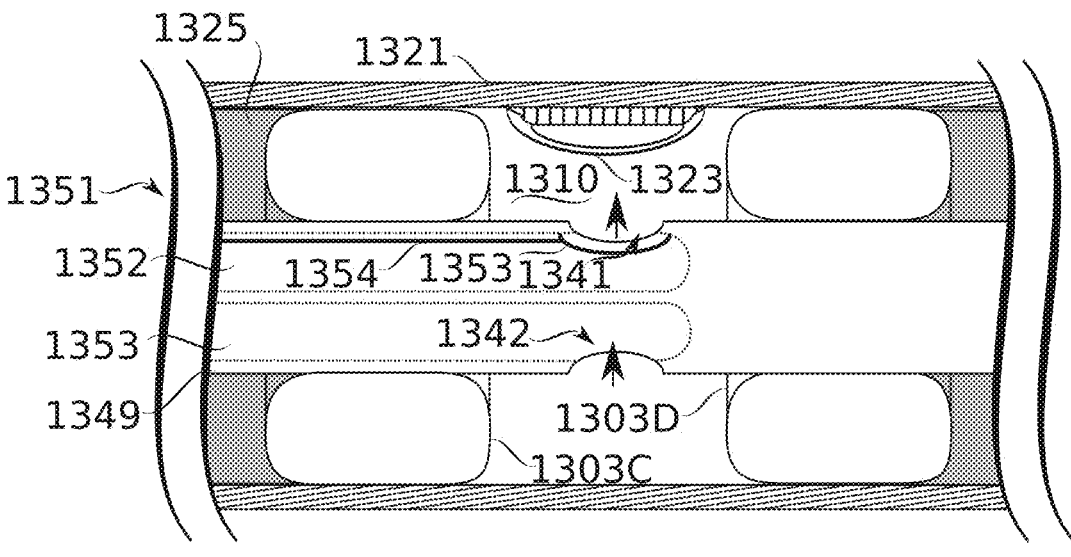
Figure 13C:
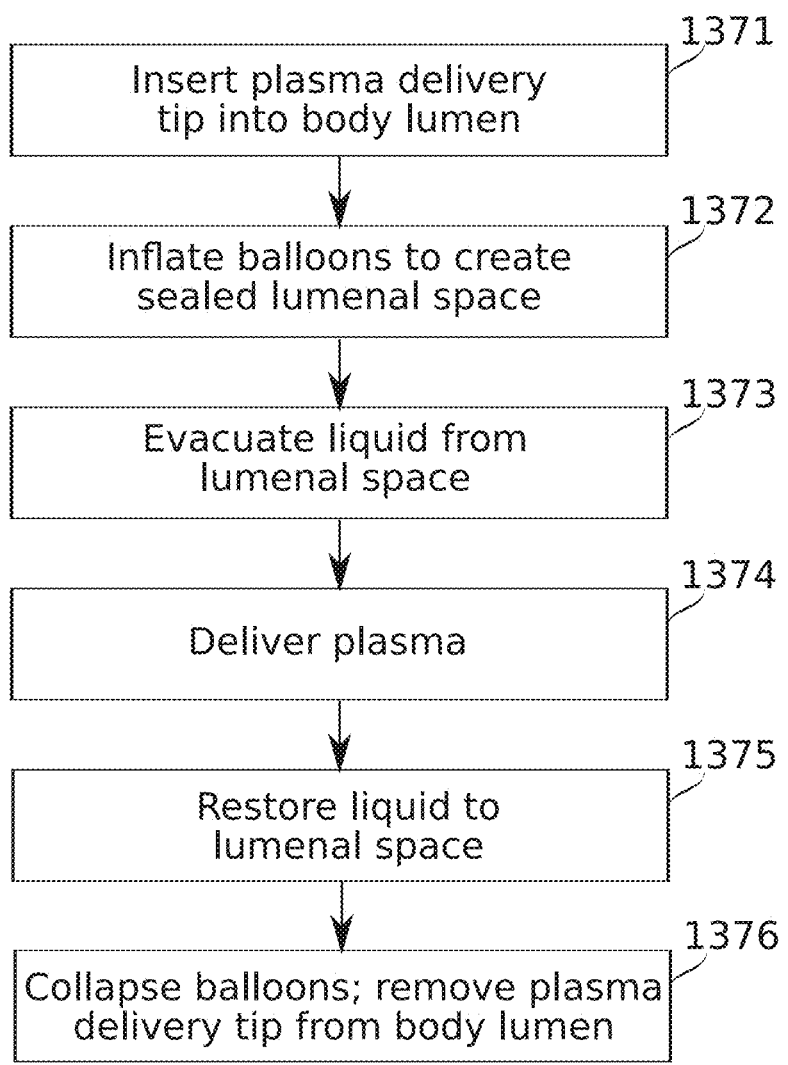
FIG. 13C is a schematic flowchart of a method of using the plasma delivery tips of FIGS. 13A-13B, according to some embodiments of the present disclosure.

Reference is now made to FIGS. 13A-13B, which schematically represent plasma delivery tips 1301, 1351 operated to deliver plasma to a target 1323 positioned within lumenal spaces 1310 established by the inflation of balloons 1303A-1303D, according to some embodiments of the present disclosure. Reference is also made to FIG. 13C, which is a schematic flowchart of a method of using the plasma delivery tips 1301, 1351 of FIGS. 13A-13B, according to some embodiments of the present disclosure.

At block 1371 (FIG. 13C), one of the plasma delivery tips 1301, 1351 is inserted within body lumenal wall 1321, which may be, for example, a lumenal wall of a blood vessel, intestine (e.g., colon), or lumen of the urinary tract.

At block 1372, in some embodiments, balloons 1303A-1303B, 1303C-1303D are inflated to seal off lumenal space 1310.

In the example of FIG. 13A, balloon 1303A is a toroidal balloon, delivered around a cylindrical body 1302 of probe tip 1301 and inflated once in position to create a seal with lumenal wall 1321. Balloon 1303B is inflated distally to a distal end of plasma delivery tip 1301, optionally using a separate device or (as shown) after distal advance of an inflation member 1305 carrying balloon 1303B out of a storage compartment 1307.

Balloons 1303C-1303D of FIG. 13B are also toroidal balloons, each carried into place on cylindrical body 1349 of plasma delivery tip 1351. Cylindrical body 1349 also comprises one or more apertures 1341, 1342 via which fluids are transported in and/or out of lumenal space 1310, and from/to fluid conduits 1352, 1353. The apertures 1341, 1342 are located on cylindrical body 1349 between the two balloons 1303C, 1303D.

After sealing off lumenal space 1310: at block 1373, in some embodiments, fluid 1325 which originally filled lumenal space 1310 is evacuated; for example by suction through fluid conduit 1311, 1353, with fluid supplied to replace the evacuated fluid via fluid conduit 1312, 1352. Additionally or alternatively, wash in of gas and/or liquid via liquid conduit 1312, 1352 forces pre-existing fluids within lumenal space 1310 out via fluid conduit 1311, 1353.

Evacuation optionally comprises a cleaning stage (using liquid such as water and/or saline), followed by a purging stage using gas. Optionally a dried gas to assist in the removal of residual moisture.

Once lumenal space 1310 is sufficiently cleared: at block 1374, in some embodiments, plasma generation begins by the delivery of voltage to electrode 306 via electrical conduit 1304 (FIG. 13A), or to electrode 1353 via electrical conduit 1354 (FIG. 13B). Lumenal space 1310 is optionally translated along the lumenal wall 1321 by advancing and/or retracting plasma delivery tip 1301, 1351. This potentially gives coverage to a larger area and/or allows corrections in case the originally established lumenal space 1310 is partially off target.

Ionization gas is carried to the lumenal space 1310 via fluid conduit 1312, 1352, and returned via fluid conduit 1311, 1353.

Generated plasma diffuses within lumenal space 1310, potentially reaching all locations, and particularly reaching the location of target 1323, which may comprise a tissue abnormality targeted for plasma treatment.

After treatment is complete: at block 1375, in some embodiments, gas is optionally replaced with liquid again (e.g., saline), before deflating balloons 1303A-1303B an (at block 1376) removing them.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting. In addition, any priority document(s) of this application is/are hereby incorporated herein by reference in its/their entirety.

What is claimed is:

1. A plasma delivery tip of a medical grade plasma generating device, the device configured for intrabody delivery of said tip through a working channel, comprising:
    a gas delivery lumen defined within a circumferential wall and having a proximal-to-distal axis, and along which a flow of ionization gas flows to a distal aperture of the gas delivery lumen;
    a discharge electrode, separated from said flow by a dielectric barrier, which transmits a high voltage to the flow of ionization gas when attached to a high voltage source; and
    a one way valve, positioned between the discharge electrode and the distal aperture to prevent proximal ingress of contamination to a longitudinal position of the discharge electrode along the proximal-to-distal axis, thereby preventing liquid contamination in a plasma generation region of the plasma delivery tip.

2. The plasma delivery tip of claim 1, wherein the valve, when closed, is also positioned to prevent ingress of liquid material through the aperture.

3. The plasma delivery tip of claim 1, wherein the plasma delivery tip comprises an expandable distal portion ending at said distal aperture, the expandable portion configured to expand in diameter for increasing a target area which is simultaneously treatable by a plasma plume emitted by the plasma delivery tip.

4. The plasma delivery tip of claim 1, wherein the valve comprises a one-way valve which opens under pressure from the flow of ionization gas.

5. The plasma delivery tip of claim 1, wherein the valve comprises an actuated valve, actuated separately from pressure from the flow of ionization gas.

6. The plasma delivery tip of claim 1, wherein the aperture of the gas delivery lumen is obliquely angled relative to the proximal-to-distal axis.

7. The plasma delivery tip of claim 1, wherein the valve comprises a leaf valve, a slit valve, or a flap valve.

8. The plasma delivery tip of claim 1, wherein the valve is configured to deflect a plasma plume generated within the flow of ionization gas by the pulses of high voltage to an angle which varies according to a degree of opening of the valve.

9. The plasma delivery tip of claim 1, comprising an outer circumferential wall surrounding and radially spaced from the circumferential wall of the gas delivery lumen to define a gap through which the ionization gas is scavenged after delivery to the discharge electrode.

10. The plasma delivery tip of claim 1, wherein the circumferential wall of the gas delivery lumen also defines a conduit through which the ionization gas is scavenged after delivery to the discharge electrode.

11. The plasma delivery tip of claim 3, wherein the expandable portion comprises an antechamber positioned along the proximal-to-distal axis between the discharge electrode and the aperture.

12. The plasma delivery tip of claim 11, wherein the antechamber expands to a have an inner diameter at least 1.5 times larger than an inner diameter of the antechamber in the collapsed configuration.

13. The plasma delivery tip of claim 2, wherein the valve comprises a calyx having one or more leaves attached on a proximal side thereof to an exterior of the plasma delivery tip.

14. The plasma delivery tip of claim 13, wherein the leaves split from each other when expanded to expose the aperture of the gas delivery lumen.

15. The plasma delivery tip of claim 12, wherein the expanded antechamber defines the aperture of the gas delivery lumen at a distal side of the antechamber.

16. The plasma delivery tip of claim 11, wherein the collapsed antechamber comprises a stiff, sharpened tip, configured to penetrate tissue.

17. The plasma delivery tip of claim 1, wherein the discharge electrode extends around at least a portion of a circumference of the gas delivery lumen.

18. The plasma delivery tip of claim 1, wherein the discharge electrode is positioned with the gas delivery lumen, and surrounded by the flow of ionization gas.

19. The plasma delivery tip of claim 1, wherein an outer diameter of the plasma delivery tip is less than 5 mm.

20. A plasma tip according to claim 17, wherein said valve is configured to leave a clear aperture for a plasma plume to pass through when open and not restrict said plume.

* * * * *